(12) United States Patent
Mouro-Chanteloup et al.

(10) Patent No.: US 10,844,109 B2
(45) Date of Patent: Nov. 24, 2020

(54) METHOD FOR PRODUCING ERYTHROCYTE PROTEINS

(71) Applicants: Institut National Transfusion Sanguine, Paris (FR); Institut National de la Sante et de la Recherche Medicale (INSERM), Paris (FR); Universite Paris Diderot Paris 7, Paris (FR)

(72) Inventors: Isabelle Mouro-Chanteloup, Saint Cloud (FR); Sandrine Genetet, Villejuif (FR)

(73) Assignees: Institut National Transfusion Sanguine (FR); Institut National de la Sante et de la Recherche Medicale (INSERM) (FR); Universite Paris Diderot Paris 7 (FR)

( * ) Notice: Subject to any disclaimer, the term of this patent is extended or adjusted under 35 U.S.C. 154(b) by 0 days.

(21) Appl. No.: 15/768,715

(22) PCT Filed: Oct. 14, 2016

(86) PCT No.: PCT/EP2016/074792
§ 371 (c)(1),
(2) Date: Apr. 16, 2018

(87) PCT Pub. No.: WO2017/064294
PCT Pub. Date: Apr. 20, 2017

(65) Prior Publication Data
US 2019/0023765 A1 Jan. 24, 2019

(30) Foreign Application Priority Data

Oct. 16, 2015 (FR) ..................................... 15 59895

(51) Int. Cl.
*C07K 14/47* (2006.01)
*G01N 33/86* (2006.01)
*C07K 14/705* (2006.01)
*C12P 21/02* (2006.01)
*G01N 33/68* (2006.01)

(52) U.S. Cl.
CPC ...... *C07K 14/70596* (2013.01); *C07K 14/705* (2013.01); *C12P 21/02* (2013.01); *G01N 33/6854* (2013.01)

(58) Field of Classification Search
CPC .............................. C07K 14/47; G01N 33/86
See application file for complete search history.

(56) References Cited

FOREIGN PATENT DOCUMENTS

| WO | 9937763 A2 | 7/1999 |
|---|---|---|
| WO | 0032632 A2 | 6/2000 |
| WO | 2005081743 A2 | 9/2005 |
| WO | 2007038755 A1 | 4/2007 |
| WO | 2008021290 A2 | 2/2008 |
| WO | 2008106660 A2 | 9/2008 |
| WO | 2012095872 A1 | 7/2012 |
| WO | 2015095854 A1 | 6/2015 |

OTHER PUBLICATIONS

Suyama et al. 2000; Surface expression of Rh-associated glycoprotein (RhAG) in nonerythroid COS-1 cells. Blood. 95(1): 336-341.*
Sachse et al. 2014; Membrane protein synthesis in cell-free systems: from bio-mimetic systems to bio-membranes. FEBS Letters. 588:2774-2781.*
Suyama et al. 1994; Rh(D) antigen expression and isolation of a new Rh(D) cDNA isoform in human erythroleukemic K562 cells.*
Huang et al. 1999; Rhmod Syndrome: A family study o the translation-initiator mutation in the Rh50 glycoprotein gene. Am. J. Hum Genet. 64: 108-117.*
Avent et al. 1988; Protein-sequence studies on Rh-related polypeptides suggest the presence of at least two groups of proteins which associated in the human rec-cell membranes. Biochem. J. 256: 1043-1046.*
Lucien et al. 2002; Antigenic and functional properties of the human red blood cell ea transporter hUT-B1. J. Biol. Chem. 277(370; 34101-34108.*
Apoil, P. A., et al., "A human monoclonal anti-D antibody which detects a nonconformation-dependent epitope on the RhD protein by immunoblot", British Journal of Haematology, Aug. 1997, vol. 98, No. 2, pp. 365-374.
Avent, N.D., et al., "The Rh blood group system: a review", Blood, Jan. 2000, vol. 95, No. 2, pp. 375-387.
Bayburt, T. H., et al., "Transducin activation by nanoscale lipid bilayers containing one and two Rhodopsins", Journal of Biological Chemistry, May 2007, vol. 282, No. 20, pp. 14875-14881.
Bernhard F. et al., "Funktionale Membranproteine durch optimierte Lipidumgebung in Nanodiscs", Biospektrum, Spektrum Akademischer Verlag, Oct. 2015, vol. 21. No. 6, pp. 640-642.
Carlson, E.D., et al., "Cell-Free Protein Synthesis: Applications Come of Age", Biotechnol Adv., Sep. 2012, vol. 30, No. 5, pp. 1185-1194.
Cartron, J. P. "RH blood group system and molecular basis of Rhdeficiency", Bailliere's Best Pract Res Clinical Haematology, Dec. 1999, vol. 12, No. 4, pp. 655-689.
Cartron, J. P., et al., "Tentative model for the mapping of D epitopes on the RhD polypeptide", Transfusion clinique et biologique,1996,vol. 3, No. 6, pp. 497-503.

(Continued)

*Primary Examiner* — Karen Cochrane Carlson
(74) *Attorney, Agent, or Firm* — Lerner, David, Littenberg, Krumholz & Mentlik, LLP

(57) ABSTRACT

The invention relates to a novel method for the synthesis of an erythrocyte protein, in which said protein is synthesized in an acellular system for the production of proteins, in the presence of at least one detergent which is non-ionic, of liposomes or of nanodiscs. The invention also relates to compositions comprising the proteins produced in this way.

Figure 1:
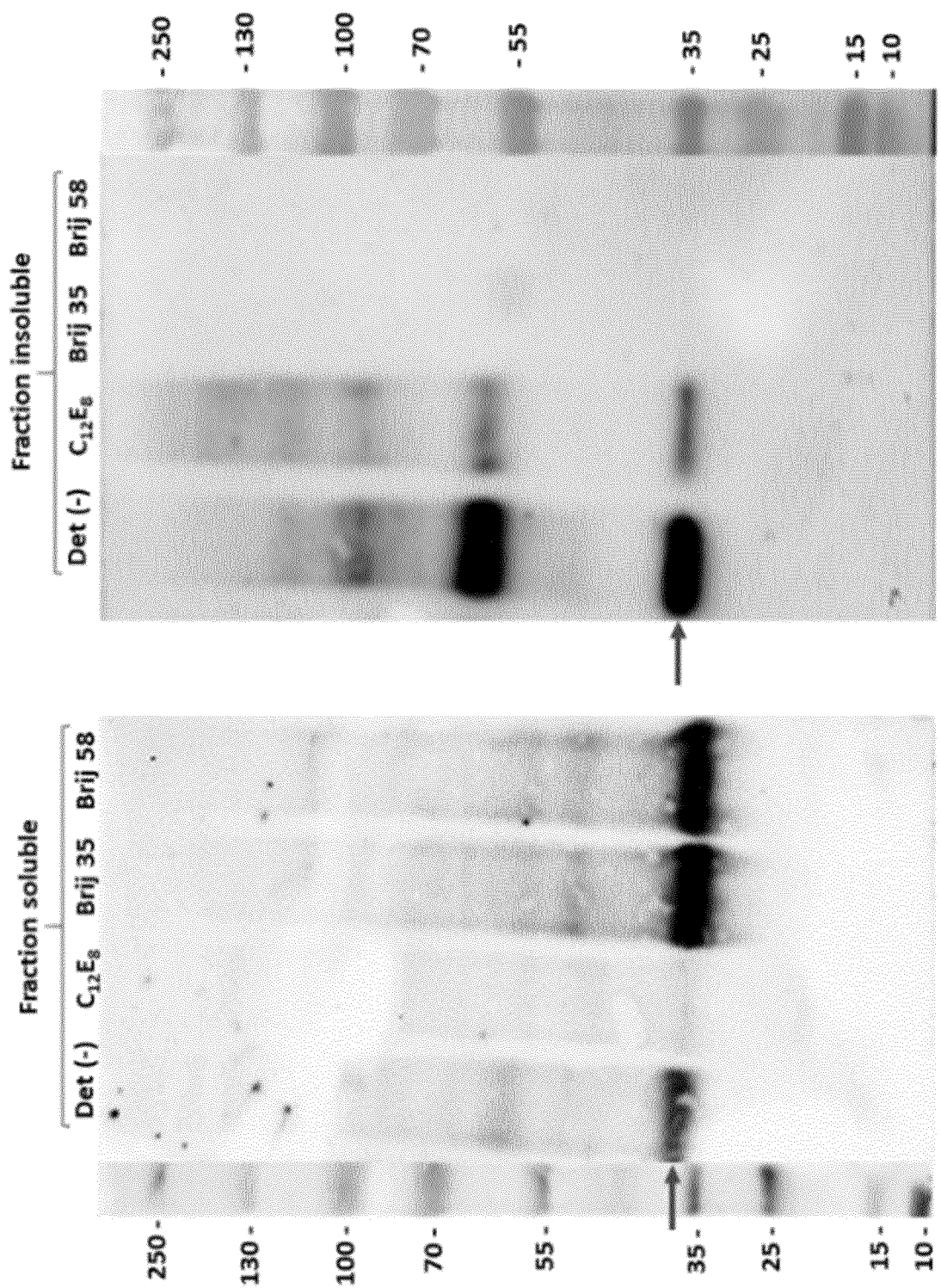

11 Claims, 7 Drawing Sheets
Specification includes a Sequence Listing.

(56) References Cited

OTHER PUBLICATIONS

Denisov, I. G., et al., "Directed self-assembly of monodisperse phospholipid bilayer Nanodiscs with controlled size", Journal of American Chemical Society, Mar. 2004, vol. 126, No. 11, pp. 3477-3487.

Goossens, D, et al., "Mice expressing RHAG and RHD human blood group genes", PLOS One, Nov. 2013, vol. 8, No. 11, pp. 80460.

Grinkova, Y.V., et al., "Engineering extended membrane scaffold proteins for CAVDV4 self-assembly of soluble nanoscale lipid bilayers", Protein Engineering, Design and Selection, Sep. 2010, vol. 23 No. 11, p. 843-848.

International Search Report for Application No. PCT/EP2016/074792 dated Feb. 16, 2017.

Mouro, I., et al., Molecular genetic basis of the human Rhesus blood group system, Nature Genetics, Sep. 1993, vol. 5, pp. 62-65.

Mouro-Chanteloup, I., A. et al., "Cell-surface expression of RhD blood group polypeptide is posttranscriptionally regulated by the RhAG glycoprotein", Blood, Aug. 2002, vol. 100, No. 3, pp. 1038-1047.

Mouro-Chanteloup, I., S. et al., "Functional reconstitution into liposomes of purified human RhCG ammonia channel", PLOS One, Jan. 2010, vol. 5, Issue 1, pp. e8921.

Rogé, J., et al., "Use of pIVEX plasmids for protein overproduction in *Escherichia coli*", Microbial Cell Factories, Jun. 2005, vol. 4, 18.

Shirokov, V. A., et al., "Continuous-exchange protein-synthesizing systems", Methods in Molecular Biology, May 2007, vol. 375, pp. 19-55.

Tippett, P., C. et al., "The Rh antigen D: partial D antigens and associated low incidence antigens", Vox Sanguinis, Apr. 1996, vol. 70, No. 3, pp. 123-131.

Gruswitz, et al., "Function of human Rh based on structure of RhCG at 2.1 Å," PNAS, May 25, 2010, pp. 9638-9643, vol. 107, No. 21.

Lux, "Anatomy of the red cell membrane skeleton: unanswered questions," Blood, Jan. 14, 2016, pp. 187-199, vol. 127, No. 2.

Mankelow, et al., "Refined views of multi-protein complexes in the erythrocyte membrane," Blood Cells Mol. Dis., Jun. 15, 2012, pp. 1-24, vol. 49, Vo. 1.

Sundquist, "Optimize Your TNT® Reticulocyte Lysate Systems Reaction," Promega Corporation, TnT® Quick Coupled Transcription/Translation System Technical Manual, TNT® T7 Quick for PCR DNA Technical Manual; [Internet] . [Accessed: Feb. 17, 2020], 12 pages. Available from: https://www.promega.com/Resources/PubHub/eNotes/Optimize%20Your%20TNT%20Reticulocyte%20Lysate%20Systems%20Reaction/.

Westhoff, et al., "Mechanism of Genetic Complementation of Ammonium Transport in Yeast by Human Erythrocyte Rh-associated Glycoprotein," The Journal of Biological Chemistry, Apr. 23, 2004, pp. 17443-17448, vol. 279, No. 17.

\* cited by examiner

SEQUENCE LISTING

<160> NUMBER OF SEQ ID NOS: 11

<210> SEQ ID NO 1
<211> LENGTH: 2549
<212> TYPE: DNA
<213> ORGANISM: Homo sapiens
<220> FEATURE:
<221> NAME/KEY: misc_feature
<223> OTHER INFORMATION: RHD

<400> SEQUENCE: 1
ggtgttggag agaggggtga tgcctggtgc tggtggaacc cctgcacaga gacggacaca 60
ggatgagctc taagtacccg cggtctgtcc ggcgctgcct gcccctctgg gccctaacac 120
tggaagcagc tctcattctc ctcttctatt tttttaccca ctatgacgct tccttagagg 180
atcaaaaggg gctcgtggca tcctatcaag ttggccaaga tctgaccgtg atggcggcca 240
ttggcttggg cttcctcacc tcgagtttcc ggagacacag ctggagcagt gtggccttca 300
acctcttcat gctggcgctt ggtgtgcagt gggcaatcct gctggacggc ttcctgagcc 360
agttcccttc tgggaaggtg gtcatcacac tgttcagtat tcggctggcc accatgagtg 420
ctttgtcggt gctgatctca gtggatgctg tcttggggaa ggtcaacttg gcgcagttgg 480
tggtgatggt gctggtggag gtgacagctt taggcaacct gaggatggtc atcagtaata 540

| | | |
|---|---|---|
| tcttcaacac agactaccac atgaacatga tgcacatcta cgtgttcgca gcctattttg | 600 |
| ggctgtctgt ggcctggtgc ctgccaaagc ctctacccga gggaacggag gataaagatc | 660 |
| agacagcaac gataccaagt ttgtctgcca tgctgggcgc cctcttcttg tggatgttct | 720 |
| ggccaagttt caactctgct ctgctgagaa gtccaatcga aggaagaat gccgtgttca | 780 |
| acacctacta tgctgtagca gtcagcgtgg tgacagccat ctcagggtca tccttggctc | 840 |
| accccaagg gaagatcagc aagacttatg tgcacagtgc ggtgttggca ggaggcgtgg | 900 |
| ctgtgggtac ctcgtgtcac ctgatccctt ctccgtggct tgccatggtg ctgggtcttg | 960 |
| tggctgggct gatctccgtc gggggagcca agtacctgcc gtttcctcat ttggctgttg | 1020 |
| gattttaagc aaaagcatcc aagaaaaaca aggcctgttc aaaaacaaga caacttcctc | 1080 |
| tcactgttgc ctgcatttgt acgtgagaaa cgctcatgac agcaaagtct ccaatgttcg | 1140 |
| cgcaggcact ggagtcagag aaaatggagt tgaatccttt ctctgccact ctttgaggag | 1200 |
| aatctcacca tttattatgc actgtagaat acaacaataa aatacagcca tgtaccacat | 1260 |
| aacaacatct tggtaaacaa cagactgcat atatgatggt ggtcatccag taagctaagg | 1320 |
| ttaatttatt attattcctt gttttttttt tttttttttt tttttttgaga tgtagtctta | 1380 |
| ctctgtcacc caggctagag tgcaatggca ccatcttggc tcactgcaac ctctacctcc | 1440 |
| tgggttcaag caaatctcct gcctcagcct ccaaagtagc tgggattaca ggcacccacc | 1500 |
| acatctggct aatttttgt attttagta aagatggggt ttcaccatgt tggccaggct | 1560 |
| gatctcaaac tcctgacctc aagtgatctg cccgcctcgg cctcccaaag tgctggaacc | 1620 |
| acaggcctga gccactgtgc ccagccttgt ttgctttttt aacagataac agtgtgctca | 1680 |
| tagaaactgc tttgacatga ctgcaatcat gtgcttcata gaaacttaat tagattatac | 1740 |
| cactagagtc ttcagatttt tatactttt tttttgaaa cggagtctca ctctgtcacc | 1800 |
| aggctggagt gcagtgccgc aatctcggct cactgcaacc tccgcctccc aggttcaagc | 1860 |
| aattctcctg cctcagcctc ccgagtagct ggaattacaa gtgcgcacta ccacacccag | 1920 |
| ctaattttg cattttact tgacaggggt tcaccatgtt ggctaggata gtttcaccag | 1980 |
| gatctcttgg cctcatgatc agcctgcctc ggcctcccaa agtgctggga ttacaggtgt | 2040 |
| gagccaccgt gcccagccta tacttccctt tttgaatacc atttggtgtt ttgaagaatt | 2100 |
| aacagctttg tgaacgtggc agtgcttgtg attcaggctt ccattgagac caaggggaga | 2160 |
| acctggttgc aggacaaaca gacggacagc gtgtggcagt gtttaaatgc tcttctgaag | 2220 |
| gctgatacga cagctctctg tgcactgatt gcatatgcat cccaagatta tattattgtt | 2280 |
| ttctactgct atgtgtcaca ctttgccaaa caggatgtgg aaaatgaata agcggttttc | 2340 |
| ttaggcactt cttaacagac aattggtcaa aatgaactcc attgcttaag aaacacataa | 2400 |
| acaccattta gtcactgaac atagctatat gtatggttgt tactatggga aatcttgttt | 2460 |
| tgccaatttt ctttgaaaat tctggcagac caaggttctt tttgtttaca taatacttga | 2520 |
| aaaataaaaa tgaacaagct aacaaacta | 2549 |

<210> SEQ ID NO 2
<211> LENGTH: 1618
<212> TYPE: DNA
<213> ORGANISM: Homo sapiens
<220> FEATURE:
<221> NAME/KEY: misc_feature
<223> OTHER INFORMATION: RHCE

<400> SEQUENCE: 2

```
atcgctccct caagccctca agtaggtgtt ggagagaggg gtgatgcctg gtgctggtgg      60 aaccctgca cagagacgga cacaggatga gctctaagta cccgcggtct gtccggcgct      120
gcctgcccct ctgggcccta acactggaag cagctctcat tctcctcttc tattttttta     180
cccactatga cgcttcctta gaggatcaaa aggggctcgt ggcatcctat caagtcggcc     240
aagatctgac cgtgatggcg gcccttggct tgggcttcct cacctcaaat ttccggagac     300
acagctggag cagtgtggcc ttcaacctct tcatgctggc gcttggtgtg cagtgggcaa     360
tcctgctgga cggcttcctg agccagttcc ctcctgggaa ggtggtcatc acactgttca     420
gtattcggct ggccaccatg agtgctatgt cggtgctgat ctcagcgggt gctgtcttgg     480
ggaaggtcaa cttggcgcag ttggtggtga tggtgctggt ggaggtgaca gctttaggca     540
ccctgaggat ggtcatcagt aatatcttca acacagacta ccacatgaac ctgaggcact     600
tctacgtgtt cgcagcctat tttgggctga ctgtggcctg gtgcctgcca aagcctctac     660
ccaagggaac ggaggataat gatcagagag caacgatacc cagtttgtct gccatgctgg     720
gcgccctctt cttgtggatg ttctggccaa gtgtcaactc tgctctgctg agaagtccaa     780
tccaaaggaa gaatgccatg ttcaacacct actatgctct agcagtcagt gtggtgacag     840
ccatctcagg gtcatccttg gctcaccccc aaaggaagat cagcatgact tatgtgcaca     900
gtgcggtgtt ggcaggaggc gtggctgtgg gtacctcgtg tcacctgatc ccttctccgt     960
ggcttgccat ggtgctgggt cttgtggctg ggctgatctc catcggggga gccaagtgcc     1020
tgccggtgtg ttgtaaccga gtgctgggga ttcaccacat ctccgtcatg cactccatct     1080
tcagcttgct gggtctgctt ggagagatca cctacattgt gctgctggtg cttcatactg     1140
tctggaacgg caatggcatg attggcttcc aggtcctcct cagcattggg gaactcagct     1200
tggccatcgt gatagctctc acgtctggtc tcctgacagg tttgctccta aatctcaaaa     1260
tatggaaagc acctcatgtg gctaaatatt ttgatgacca gtttttctgg aagtttcctc     1320
atttggctgt tggattttaa gcaaaagcat ccaagaaaaa caaggcctgt tcaaaaacaa     1380
gacaacttcc tctcactgtt gcctgcattt gtacgtgaga acgctcatg acagcaaagt      1440 ctccttatgt ataatgaaac aaggtcagag acagatttga tattaaaaaa ttaaagacta     1500
aaaacttagt ttaagagtca atttaataag tttaaaataa atgtttagtt tcattaggat     1560
gatgctatca atattttctt ggttacagac acattattaa agttttgggt taattttta      1618
```

<210> SEQ ID NO 3
<211> LENGTH: 3836
<212> TYPE: DNA
<213> ORGANISM: Homo sapiens
<220> FEATURE:
<221> NAME/KEY: misc_feature
<223> OTHER INFORMATION: RHAG

<400> SEQUENCE: 3

```
gttcttatca acatctcaca gcctgtgaag ctctcagtgt gcctctgtcc tttgccacaa      60
acatgaggtt cacattccct ctcatggcta tagtcctgga aattgccatg attgtttttat    120 ttggattatt tgttgagtat gaaacggacc agactgttct cgagcagctc aacatcacca     180
agccaacaga catgggcata ttctttgagt tatatcctct gttccaagat gtacatgtta     240
tgatatttgt tgggttttggc ttcctcatga ccttcctgaa gaaatatggc ttcagcagtg    300
tgggtatcaa cctactcgtt gctgctttgg gcctccagtg gggcactatt gtacagggaa     360
tcctgcaaag ccagggacag aaatttaaca ttggaatcaa aacatgata aatgcagact      420
```

```
tcagtgcagc cacagttctg atatcttttg gagctgtcct gggaaaaacg agccccaccc      480
aaatgctgat gttcttatca acatctcaca gcctgtgaag ctctcagtgt gcctctgtcc      540
tttgccacaa acatgaggtt cacattccct ctcatggcta tagtcctgga aattgccatg      600
attgttttat ttggattatt tgttgagtat gaaacggacc agactgttct cgagcagctc      660
aacatcacca agccaacaga catgggcata ttctttgagt tatatcctct gttccaagat      720
gtacatgtta tgatatttgt tgggtttggc ttcctcatga ccttcctgaa gaaatatggc      780
ttcagcagtg tgggtatcaa cctactcgtt gctgctttgg gcctccagtg gggcactatt      840
gtacagggaa tcctgcaaag ccagggacag aaatttaaca ttggaatcaa aaacatgata      900
aatgcagact tcagtgcagc cacagttctg atatcttttg gagctgtcct gggaaaaacg      960
agccccaccc aaatgctgat catgacaatt ttagaaattg ttttctttgc ccacaatgaa     1020
tacctggtta gtgaaatatt taaggcctct gacattggag catcaatgac gatccatgcc     1080
tttggggcct actttggctt ggctgtagca ggcatcttgt atcgatctgg actgagaaag     1140 ggcatgaaa atgaagagtc cgcatactac tcagacttgt ttgcaatgat tgggactctc     1200
tttctgtgga tgttttggcc cagctttaac tcggccattg ctgaacctgg agacaaacag     1260
tgcagggcca ttgtaaacac gtacttctct ctcgctgcct gtgtgctcac agcctttgcc     1320
ttctccagcc tagtggagca ccgaggcaag ctcaacatgg ttcacattca gaatgccacc     1380
cttgctggag gagttgctgt gggcacttgt gcggatatgg caattcaccc atttggttct     1440
atgattattg ggagcattgc aggaatggtc tctgtgcttg atacaagttt cctgactcca     1500
cttttactac taaactgag gatccatgat acatgtgggg tccataacct ccacggctta     1560
cctggtgtag tgggaggcct tgcaggcatt gtggcagtag caatgggcgc ctccaacacg     1620
tctatggcca tgcaggcagc tgcactgggt tcctctatcg gaacagcagt tgttggaggt     1680
ctgatgacag gtttaattct aaagttgcct ctctggggac agccatctga ccagaactgc     1740
tatgatgatt ctgtttattg gaaggtccct aagacgagat aacttgacaa tcagttccat     1800
ggacatggtg accacagcca gctgaacct gaagtctaaa caccattcct gctctccagc     1860
ttcctttccc attatccaga atcaagtcca aataaacaaa aagggagtaa ccaaagagag     1920
tatggaccag agtgaataga tcctaagtcc caaatggcca gtgtaaaaat gtccttatgt     1980
ctgatgctgt ctcttgctct tcaatgatta attgagggga tgttactcat aaaacagata     2040
atcaaataga tcttctccag gattcccaaa aagcttttgg cagtgagtaa atacagagta     2100
aacatgtcag tttcttaatg tagacactat gtcttcaatc ccaaaaatta taaaactgaa     2160
acccatgaag caagaataga tgtgagaaat ctatgtaaaa aaataattaa agaaatgcat     2220
gtgtgtaaag tagtaatatg atgattttag gtagtgcttt ttatttaaa aatagtctag     2280 ttagtaatgt tgtatccttg catgaatatt attcttaatt ccttttgcat gttgactatt     2340
tgcaacgagc tcaaatgcta tctgatcaaa gtctattttg cataaaatgt ccaataatta     2400
aatattgtta taaaataaaa aaaaaaaaaa aaaaaaaaa aaagacattg gagcatcaat     2460
gacgatccat gcctttgggg cctactttgg cttggctgta gcaggcatct tgtatcgatc     2520
tggactgaga aaggggcatg aaaatgaaga gtccgcatac tactcagact tgtttgcaat     2580
gattgggact ctcttttctgt ggatgttttg gcccagcttt aactcggcca ttgctgaacc     2640
tggagacaaa cagtgcaggg ccattgtaaa cacgtacttc tctctcgctg cctgtgtgct     2700
cacagccttt gccttctcca gcctagtgga gcaccgaggc aagctcaaca tggttcacat     2760
```

-continued

| | |
|---|---|
| tcagaatgcc acccttgctg gaggagttgc tgtgggcact tgtgcggata tggcaattca | 2820 |
| cccatttggt tctatgatta ttgggagcat tgcaggaatg gtctctgtgc ttggatacaa | 2880 |
| gttcctgact ccacttttta ctactaaact gaggatccat gatacatgtg gggtccataa | 2940 |
| cctccacggc ttacctggtg tagtggggagg ccttgcaggc attgtggcag tagcaatggg | 3000 |
| cgcctccaac acgtctatgg ccatgcaggc agctgcactg ggttcctcta tcggaacagc | 3060 |
| agttgttgga ggtctgatga caggtttaat tctaaagttg cctctctggg acagccatc | 3120 |
| tgaccagaac tgctatgatg attctgttta ttggaaggtc cctaagacga gataacttga | 3180 |
| caatcagttc catggacatg gtgaccacag ccagctggaa cctgaagtct aaacaccatt | 3240 |
| cctgctctcc agcttccttt cccattatcc agaatcaagt ccaaataaac aaaaagggag | 3300 |
| taaccaaaga gagtatggac cagagtgaat agatcctaag tcccaaatgg ccagtgtaaa | 3360 |
| aatgtcctta tgtctgatgc tgtctcttgc tcttcaatga ttaattgagg ggatgttact | 3420 |
| cataaaacag ataatcaaat agatcttctc caggattccc aaaaagcttt tggcagtgag | 3480 |
| taaatacaga gtaaacatgt cagtttctta atgtagacac tatgtcttca atcccaaaaa | 3540 |
| ttataaaact gaaacccatg aagcaagaat agatgtgaga aatctatgta aaaaaataat | 3600 |
| taagaaaatg catgtgtgta aagtagtaat atgatgattt taggtagtgc ttttttatttt | 3660 |
| aaaaatagtc tagttagtaa tgttgtatcc ttgcatgaat attattctta attccttttg | 3720 |
| catgttgact atttgcaacg agctcaaatg ctatctgatc aaagtctatt ttgcataaaa | 3780 |
| tgtccaataa ttaaatattg ttataaaata aaaaaaaaaa aaaaaaaaaa aaaaaa | 3836 |

<210> SEQ ID NO 4
<211> LENGTH: 4129
<212> TYPE: DNA
<213> ORGANISM: Homo sapiens
<220> FEATURE:
<221> NAME/KEY: misc_feature
<223> OTHER INFORMATION: SLC14A1

<400> SEQUENCE: 4

| | |
|---|---|
| acacagagca gagtgggget ctgagtatat aactgttagg tgcctccctc cagcaccatc | 60 |
| tcctgagaag cactctccct tgtcgtggag gtgggcaaat ctttatcagc cactgccttc | 120 |
| tgctgccagg aagccagcta gagtggtctt taaagaaaac tgggcatctc ctgctactta | 180 |
| aaatcaaaaa ctacctaaaa taaagattat aaaaagtaa ggatgaatgg acggtctttg | 240 |
| attggcggcg ctggtgacgc ccgtcatggt cctgtttgga aggaccctt tggaactaaa | 300 |
| gctggtgaca cagcgcgcag aggcatcgcc cggctaagct tggccctggc agatgggtcg | 360 |
| caggaacagg agccagagga agagatagcc atggaggaca gccccactat ggttagagtg | 420 |
| gacagcccca ctatggttag gggtgaaaac caggtttcgc catgtcaagg gagaaggtgc | 480 |
| ttccccaaag ctcttggcta tgtcaccggt gacatgaaag aacttgccaa ccagcttaaa | 540 |
| gacaaacccg tggtgctcca gttcattgac tggattctcc ggggcatatc ccaagtggtg | 600 |
| ttcgtcaaca accccgtcag tggaatcctg attctggtag gacttcttgt tcagaacccc | 660 |
| tggtgggctc tcactggctg gctgggaaca gtggtctcca ctctgatggc cctcttgctc | 720 |
| agccaggaca ggtcattaat agcatctggg ctctatggct acaatgccac cctggtggga | 780 |
| gtactcatgg ctgtcttttc ggacaaggga gactatttct ggtggctgtt actccctgta | 840 |
| tgtgctatgt ccatgacttg cccaattttc tcaagtgcat tgaattccat gctcagcaaa | 900 |
| tgggacctcc ccgtcttcac cctcccttc aacatggcgt tgtcaatgta cctttcagcc | 960 |

```
acaggacatt acaatccatt cttccagcc aaactggtca tacctataac tacagctcca    1020
aatatctcct ggtctgacct cagtgccctg gagttgttga aatctatacc agtgggagtt    1080
ggtcagatct atggctgtga taatccatgg acaggggca ttttcctggg agccatccta    1140
ctctcctccc cactcatgtg cctgcatgct gccataggat cattgctggg catagcagcg    1200
ggactcagtc tttcagcccc atttgaggac atctactttg gactctgggg tttcaacagc    1260
tctctggcct gcattgcaat gggaggaatg ttcatggcgc tcacctggca aacccacctc    1320
ctggctcttg gctgtgccct gttcacggcc tatcttggag tcggcatggc aaactttatg    1380
gctgaggttg gattgccagc ttgtacctgg cccttctgtt tggccacgct attgttcctc    1440
atcatgacca caaaaaattc caacatctac aagatgcccc tcagtaaagt tacttatcct    1500
gaagaaaacc gcatcttcta cctgcaagcc aagaaaagaa tggtggaaag cccttttgtga   1560
gaacaagccc catttgcagc catggtcacg agtcatttct gcctgactgc tccagctaac    1620
ttccagggtc tcagcaaact gctgtttttc acgagtatca actttcatac tgacgcgtct    1680
gtaatctgtt cttatgctca tttgtattt tcctttcaac tccaggaata tccttgagca    1740
tatgagagtc acatccaggt gatgtgctct ggtatggaat ttgaaacccc aatgggggcct   1800
tggcactaag actggaatgt atataaagtc aaagtgctcc aacagaagga ggaagtgaaa    1860
acaaactatt agtatttatt gatattcttg gtgtttagct ggctcgatga tgttaacagt    1920
attaaaaatt aaacccata aaccaactaa gccttatgga attcacagtc acaaaatcga     1980
agttaatcca gaattctgtg ataagcagct tggcttttt ttaaatcaa tgcaagttac      2040
acattatagc cagaatctgt atcacagagg tgcaagctga cagcagagct cagtccccac    2100
ttcctgcaaa caatggcctg caccctatcc cttgtgtgtg tgacattctc tcatgggaca    2160
atgttggggt ttttcagact gacaggactg caagagggag aaaggaattt tgtcaatcaa    2220
aattattctg tattgcaact tttctcagag attgcaaagg attttttagg tagagattat    2280
ttttccttat gaaaaatgat ctgtttttaaa tgagataaaa taggagaagt tcctggctta   2340
acctgttctt acatattaaa gaaaagttac ttactgtatt tatgaaatac tcagcttagg    2400
cattttact ttaaccccta aattgatttt gtaaatgcca caaatgcata gaattgttac     2460
caacctccaa agggctcttt aaaatcatat ttttattca tttgaggatg tcttataaag     2520
actgaaggca aagtcagat tgcttacggg tgttattttt ataagttgtt gaattcctta    2580
atttaaaaaa gctcattatt ttttgcacac tcacaatatt ctctctcaga aatcaatggc    2640
atttgaacca ccaaaaagaa ataaagggct gagtgcggtg gctcacgcct gtaatcccag    2700
cactttgggg agcccaggcg ggcagattgc ttgaacccag gagttcaaga ccagcctggg    2760
cagcatggtg aaaccctgta tctacaaaaa atacaaaaat tagccaggca tggtggtggg    2820
tgcctgtagt tccagctact tgggaggctg aggtgggaaa atgacttgag cccaggagga    2880
ggaggctgca gtgagctaag attgcaccac tgcactccaa cctgggcgac aagagtgaaa    2940
ctgtgtctct caaaaaaaaa aaaaaacaaa caaaaacaaa acaaaacaa aacaaaacaa     3000
aacaaaacag gtaaggattc ccctgttttc ctctctttaa ttttaaagtt atcagttccg    3060
taaagtctct gtaaccaaac atactgaaga cagcaacaga agtcacgttc agggactggc    3120
tcacacctgt aatcccagca ctttgggaga tggaggtaaa aggatctctt gagcccagga    3180
gttcaagacc agcttgggca acatagcaag actccatctc ttaaaaaata aaatagtaa     3240
cattagccag gtgtagcagc acacatctgc agcagctact caggaggctg aggtggaaag    3300
atcgcttgtg cacagaagtt cgaggctgca gtgagctata tgatcatgtc actgcactcc    3360
```

-continued

```
agcctgtgtg accgagcaag accctatctc aaaaaaatta attaattaat taattaatta    3420
atttaaaaag gaagtcatgt tcatttactt tccacttcag tgtgtatcgt gtagtatttt    3480
ggaggttgga aagtgaaacg taggaatcct gaagattttt tccacttcta gtttgcagtg    3540
ctcagtgcac aatatacatt ttgctgaatg aataaacaga aatagggaag taaacctaca    3600
aatattttag ggagaagctc acttcttcct tttctcagga aaccaagcaa gcaaacatat    3660
cgttccaatt ttaaaaccca gtgaccaaag cctttggaac tatgaatttg caactgtcat    3720
aggtttatgg atattgctgt ggagaagctc aattttcagt gtttgaactg aaccctttct    3780
tgttagggaa cgtgtgaaag aagaattgtg gggaaaaaaa agcaagcata accaaagatc    3840
atcagcagtg aagaatctag gctgtggctg agagaaccag aggcctctaa aatggacccg    3900
agtcgatctt cagaacaggg atctaccatg caggagcttc ttgtgctcac acaaatctgt    3960
aaatgggaac attgtacatt gtcgaattta aatgatatta attttctcaa gctattttg     4020 ttactatttt cctaaaattg aatatttgca gggagcactt atacttttc ctaatgtctg     4080 tataacaaat ttctatgcaa gtacatgaat aaattatgct cacagctca                4129
```

```
<210> SEQ ID NO 5
<211> LENGTH: 321
<212> TYPE: PRT
<213> ORGANISM: Homo sapiens
<220> FEATURE:
<221> NAME/KEY: SITE
<222> LOCATION: (1)..(321)
<223> OTHER INFORMATION: RhD

<400> SEQUENCE: 5
```

Met Ser Ser Lys Tyr Pro Arg Ser Val Arg Arg Cys Leu Pro Leu Trp
1               5                   10                  15

Ala Leu Thr Leu Glu Ala Ala Leu Ile Leu Leu Phe Tyr Phe Phe Thr
            20                  25                  30

His Tyr Asp Ala Ser Leu Glu Asp Gln Lys Gly Leu Val Ala Ser Tyr
        35                  40                  45

Gln Val Gly Gln Asp Leu Thr Val Met Ala Ala Ile Gly Leu Gly Phe
    50                  55                  60

Leu Thr Ser Ser Phe Arg Arg His Ser Trp Ser Ser Val Ala Phe Asn
65                  70                  75                  80

Leu Phe Met Leu Ala Leu Gly Val Gln Trp Ala Ile Leu Leu Asp Gly
                85                  90                  95

Phe Leu Ser Gln Phe Pro Ser Gly Lys Val Val Ile Thr Leu Phe Ser
            100                 105                 110

Ile Arg Leu Ala Thr Met Ser Ala Leu Ser Val Leu Ile Ser Val Asp
        115                 120                 125

Ala Val Leu Gly Lys Val Asn Leu Ala Gln Leu Val Val Met Val Leu
    130                 135                 140

Val Glu Val Thr Ala Leu Gly Asn Leu Arg Met Val Ile Ser Asn Ile
145                 150                 155                 160

Phe Asn Thr Asp Tyr His Met Asn Met Met His Ile Tyr Val Phe Ala
                165                 170                 175

Ala Tyr Phe Gly Leu Ser Val Ala Trp Cys Leu Pro Lys Pro Leu Pro
            180                 185                 190

Glu Gly Thr Glu Asp Lys Asp Gln Thr Ala Thr Ile Pro Ser Leu Ser
        195                 200                 205

Ala Met Leu Gly Ala Leu Phe Leu Trp Met Phe Trp Pro Ser Phe Asn

-continued

```
                210                 215                 220
Ser Ala Leu Leu Arg Ser Pro Ile Glu Arg Lys Asn Ala Val Phe Asn
225                 230                 235                 240

Thr Tyr Tyr Ala Val Ala Val Ser Val Val Thr Ala Ile Ser Gly Ser
                245                 250                 255

Ser Leu Ala His Pro Gln Gly Lys Ile Ser Lys Thr Tyr Val His Ser
                260                 265                 270

Ala Val Leu Ala Gly Gly Val Ala Val Gly Thr Ser Cys His Leu Ile
                275                 280                 285

Pro Ser Pro Trp Leu Ala Met Val Leu Gly Leu Val Ala Gly Leu Ile
                290                 295                 300

Ser Val Gly Gly Ala Lys Tyr Leu Pro Phe Pro His Leu Ala Val Gly
305                 310                 315                 320

Phe
```

<210> SEQ ID NO 6
<211> LENGTH: 417
<212> TYPE: PRT
<213> ORGANISM: Homo sapiens
<220> FEATURE:
<221> NAME/KEY: SITE
<222> LOCATION: (1)..(417)
<223> OTHER INFORMATION: RhCE

<400> SEQUENCE: 6

```
Met Ser Ser Lys Tyr Pro Arg Ser Val Arg Arg Cys Leu Pro Leu Trp
1               5                   10                  15

Ala Leu Thr Leu Glu Ala Ala Leu Ile Leu Leu Phe Tyr Phe Phe Thr
                20                  25                  30

His Tyr Asp Ala Ser Leu Glu Asp Gln Lys Gly Leu Val Ala Ser Tyr
            35                  40                  45

Gln Val Gly Gln Asp Leu Thr Val Met Ala Ala Leu Gly Leu Gly Phe
        50                  55                  60

Leu Thr Ser Asn Phe Arg Arg His Ser Trp Ser Ser Val Ala Phe Asn
65              70                  75                  80

Leu Phe Met Leu Ala Leu Gly Val Gln Trp Ala Ile Leu Leu Asp Gly
                85                  90                  95

Phe Leu Ser Gln Phe Pro Pro Gly Lys Val Val Ile Thr Leu Phe Ser
            100                 105                 110

Ile Arg Leu Ala Thr Met Ser Ala Met Ser Val Leu Ile Ser Ala Gly
        115                 120                 125

Ala Val Leu Gly Lys Val Asn Leu Ala Gln Leu Val Val Met Val Leu
    130                 135                 140

Val Glu Val Thr Ala Leu Gly Thr Leu Arg Met Val Ile Ser Asn Ile
145                 150                 155                 160

Phe Asn Thr Asp Tyr His Met Asn Leu Arg His Phe Tyr Val Phe Ala
                165                 170                 175

Ala Tyr Phe Gly Leu Thr Val Ala Trp Cys Leu Pro Lys Pro Leu Pro
            180                 185                 190

Lys Gly Thr Glu Asp Asn Asp Gln Arg Ala Thr Ile Pro Ser Leu Ser
        195                 200                 205

Ala Met Leu Gly Ala Leu Phe Leu Trp Met Phe Trp Pro Ser Val Asn
    210                 215                 220

Ser Ala Leu Leu Arg Ser Pro Ile Gln Arg Lys Asn Ala Met Phe Asn
225                 230                 235                 240
```

```
Thr Tyr Tyr Ala Leu Ala Val Ser Val Val Thr Ala Ile Ser Gly Ser
                245                 250                 255

Ser Leu Ala His Pro Gln Arg Lys Ile Ser Met Thr Tyr Val His Ser
            260                 265                 270

Ala Val Leu Ala Gly Gly Val Ala Val Gly Thr Ser Cys His Leu Ile
        275                 280                 285

Pro Ser Pro Trp Leu Ala Met Val Leu Gly Leu Val Ala Gly Leu Ile
    290                 295                 300

Ser Ile Gly Gly Ala Lys Cys Leu Pro Val Cys Cys Asn Arg Val Leu
305                 310                 315                 320

Gly Ile His His Ile Ser Val Met His Ser Ile Phe Ser Leu Leu Gly
                325                 330                 335

Leu Leu Gly Glu Ile Thr Tyr Ile Val Leu Leu Val Leu His Thr Val
            340                 345                 350

Trp Asn Gly Asn Gly Met Ile Gly Phe Gln Val Leu Leu Ser Ile Gly
        355                 360                 365

Glu Leu Ser Leu Ala Ile Val Ile Ala Leu Thr Ser Gly Leu Leu Thr
    370                 375                 380

Gly Leu Leu Leu Asn Leu Lys Ile Trp Lys Ala Pro His Val Ala Lys
385                 390                 395                 400

Tyr Phe Asp Asp Gln Val Phe Trp Lys Phe Pro His Leu Ala Val Gly
                405                 410                 415

Phe

<210> SEQ ID NO 7
<211> LENGTH: 409
<212> TYPE: PRT
<213> ORGANISM: Homo sapiens
<220> FEATURE:
<221> NAME/KEY: SITE
<222> LOCATION: (1)..(409)
<223> OTHER INFORMATION: RhAG

<400> SEQUENCE: 7

Met Arg Phe Thr Phe Pro Leu Met Ala Ile Val Leu Glu Ile Ala Met
1               5                   10                  15

Ile Val Leu Phe Gly Leu Phe Val Glu Tyr Glu Thr Asp Gln Thr Val
            20                  25                  30

Leu Glu Gln Leu Asn Ile Thr Lys Pro Thr Asp Met Gly Ile Phe Phe
        35                  40                  45

Glu Leu Tyr Pro Leu Phe Gln Asp Val His Val Met Ile Phe Val Gly
    50                  55                  60

Phe Gly Phe Leu Met Thr Phe Leu Lys Lys Tyr Gly Phe Ser Ser Val
65                  70                  75                  80

Gly Ile Asn Leu Leu Val Ala Ala Leu Gly Leu Gln Trp Gly Thr Ile
                85                  90                  95

Val Gln Gly Ile Leu Gln Ser Gln Gly Gln Lys Phe Asn Ile Gly Ile
            100                 105                 110

Lys Asn Met Ile Asn Ala Asp Phe Ser Ala Ala Thr Val Leu Ile Ser
        115                 120                 125

Phe Gly Ala Val Leu Gly Lys Thr Ser Pro Thr Gln Met Leu Ile Met
    130                 135                 140

Thr Ile Leu Glu Ile Val Phe Phe Ala His Asn Glu Tyr Leu Val Ser
145                 150                 155                 160

Glu Ile Phe Lys Ala Ser Asp Ile Gly Ala Ser Met Thr Ile His Ala
                165                 170                 175
```

-continued

```
Phe Gly Ala Tyr Phe Gly Leu Ala Val Ala Gly Ile Leu Tyr Arg Ser
            180                 185                 190
Gly Leu Arg Lys Gly His Glu Asn Glu Glu Ser Ala Tyr Tyr Ser Asp
            195                 200                 205
Leu Phe Ala Met Ile Gly Thr Leu Phe Leu Trp Met Phe Trp Pro Ser
    210                 215                 220
Phe Asn Ser Ala Ile Ala Glu Pro Gly Asp Lys Gln Cys Arg Ala Ile
225                 230                 235                 240
Val Asn Thr Tyr Phe Ser Leu Ala Ala Cys Val Leu Thr Ala Phe Ala
                245                 250                 255
Phe Ser Ser Leu Val Glu His Arg Gly Lys Leu Asn Met Val His Ile
            260                 265                 270
Gln Asn Ala Thr Leu Ala Gly Gly Val Ala Val Gly Thr Cys Ala Asp
            275                 280                 285
Met Ala Ile His Pro Phe Gly Ser Met Ile Ile Gly Ser Ile Ala Gly
    290                 295                 300
Met Val Ser Val Leu Gly Tyr Lys Phe Leu Thr Pro Leu Phe Thr Thr
305                 310                 315                 320
Lys Leu Arg Ile His Asp Thr Cys Gly Val His Asn Leu His Gly Leu
                325                 330                 335
Pro Gly Val Val Gly Gly Leu Ala Gly Ile Val Ala Val Ala Met Gly
            340                 345                 350
Ala Ser Asn Thr Ser Met Ala Met Gln Ala Ala Leu Gly Ser Ser
            355                 360                 365
Ile Gly Thr Ala Val Val Gly Gly Leu Met Thr Gly Leu Ile Leu Lys
    370                 375                 380
Leu Pro Leu Trp Gly Gln Pro Ser Asp Gln Asn Cys Tyr Asp Asp Ser
385                 390                 395                 400
Val Tyr Trp Lys Val Pro Lys Thr Arg
                405
```

<210> SEQ ID NO 8
<211> LENGTH: 445
<212> TYPE: PRT
<213> ORGANISM: Homo sapiens
<220> FEATURE:
<221> NAME/KEY: SITE
<222> LOCATION: (1)..(445)
<223> OTHER INFORMATION: UTB

<400> SEQUENCE: 8

```
Met Asn Gly Arg Ser Leu Ile Gly Gly Ala Gly Asp Ala Arg His Gly
1               5                   10                  15
Pro Val Trp Lys Asp Pro Phe Gly Thr Lys Ala Gly Asp Ala Ala Arg
            20                  25                  30
Arg Gly Ile Ala Arg Leu Ser Leu Ala Leu Ala Asp Gly Ser Gln Glu
        35                  40                  45
Gln Glu Pro Glu Glu Glu Ile Ala Met Glu Asp Ser Pro Thr Met Val
    50                  55                  60
Arg Val Asp Ser Pro Thr Met Val Arg Gly Glu Asn Gln Val Ser Pro
65                  70                  75                  80
Cys Gln Gly Arg Arg Cys Phe Pro Lys Ala Leu Gly Tyr Val Thr Gly
                85                  90                  95
Asp Met Lys Glu Leu Ala Asn Gln Leu Lys Asp Lys Pro Val Val Leu
            100                 105                 110
```

-continued

```
Gln Phe Ile Asp Trp Ile Leu Arg Gly Ile Ser Gln Val Phe Val
            115                 120                 125

Asn Asn Pro Val Ser Gly Ile Leu Ile Leu Val Gly Leu Leu Val Gln
130                 135                 140

Asn Pro Trp Trp Ala Leu Thr Gly Trp Leu Gly Thr Val Val Ser Thr
145                 150                 155                 160

Leu Met Ala Leu Leu Leu Ser Gln Asp Arg Ser Leu Ile Ala Ser Gly
                165                 170                 175

Leu Tyr Gly Tyr Asn Ala Thr Leu Val Gly Val Leu Met Ala Val Phe
            180                 185                 190

Ser Asp Lys Gly Asp Tyr Phe Trp Trp Leu Leu Leu Pro Val Cys Ala
        195                 200                 205

Met Ser Met Thr Cys Pro Ile Phe Ser Ser Ala Leu Asn Ser Met Leu
    210                 215                 220

Ser Lys Trp Asp Leu Pro Val Phe Thr Leu Pro Phe Asn Met Ala Leu
225                 230                 235                 240

Ser Met Tyr Leu Ser Ala Thr Gly His Tyr Asn Pro Phe Phe Pro Ala
                245                 250                 255

Lys Leu Val Ile Pro Ile Thr Thr Ala Pro Asn Ile Ser Trp Ser Asp
            260                 265                 270

Leu Ser Ala Leu Glu Leu Leu Lys Ser Ile Pro Val Gly Val Gly Gln
        275                 280                 285

Ile Tyr Gly Cys Asp Asn Pro Trp Thr Gly Gly Ile Phe Leu Gly Ala
    290                 295                 300

Ile Leu Leu Ser Ser Pro Leu Met Cys Leu His Ala Ala Ile Gly Ser
305                 310                 315                 320

Leu Leu Gly Ile Ala Ala Gly Leu Ser Leu Ser Ala Pro Phe Glu Asp
                325                 330                 335

Ile Tyr Phe Gly Leu Trp Gly Phe Asn Ser Ser Leu Ala Cys Ile Ala
            340                 345                 350

Met Gly Gly Met Phe Met Ala Leu Thr Trp Gln Thr His Leu Leu Ala
        355                 360                 365

Leu Gly Cys Ala Leu Phe Thr Ala Tyr Leu Gly Val Gly Met Ala Asn
    370                 375                 380

Phe Met Ala Glu Val Gly Leu Pro Ala Cys Thr Trp Pro Phe Cys Leu
385                 390                 395                 400

Ala Thr Leu Leu Phe Leu Ile Met Thr Thr Lys Asn Ser Asn Ile Tyr
                405                 410                 415

Lys Met Pro Leu Ser Lys Val Thr Tyr Pro Glu Glu Asn Arg Ile Phe
            420                 425                 430

Tyr Leu Gln Ala Lys Lys Arg Met Val Glu Ser Pro Leu
        435                 440                 445

<210> SEQ ID NO 9
<211> LENGTH: 201
<212> TYPE: PRT
<213> ORGANISM: Homo sapiens
<220> FEATURE:
<221> NAME/KEY: SITE
<222> LOCATION: (1)..(201)
<223> OTHER INFORMATION: MSP1

<400> SEQUENCE: 9

Gly Leu Lys Leu Leu Ser Asn Trp Asp Ser Val Thr Ser Thr Phe Ser
1               5                   10                  15

Lys Leu Arg Glu Gln Leu Gly Pro Val Thr Gln Glu Phe Trp Asp Asn
```

```
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 10
<211> LENGTH: 211
<212> TYPE: PRT
<213> ORGANISM: Homo sapiens
<220> FEATURE:
<221> NAME/KEY: SITE
<222> LOCATION: (1)..(211)
<223> OTHER INFORMATION: MSP1D1

<400> SEQUENCE: 10

Gly His His His His His His Asp Tyr Asp Ile Pro Thr Thr Glu
1               5                   10                  15

Asn Leu Tyr Phe Gln Gly Ser Thr Phe Ser Lys Leu Arg Glu Gln Leu
                20                  25                  30

Gly Pro Val Thr Gln Glu Phe Trp Asp Asn Leu Glu Lys Glu Thr Glu
            35                  40                  45

Gly Leu Arg Gln Glu Met Ser Lys Asp Leu Glu Glu Val Lys Ala Lys
    50                  55                  60

Val Gln Pro Tyr Leu Asp Asp Phe Gln Lys Lys Trp Gln Glu Glu Met
65                  70                  75                  80

Glu Leu Tyr Arg Gln Lys Val Glu Pro Leu Arg Ala Glu Leu Gln Glu
                85                  90                  95

Gly Ala Arg Gln Lys Leu His Glu Leu Gln Glu Lys Leu Ser Pro Leu
            100                 105                 110

Gly Glu Glu Met Arg Asp Arg Ala Arg Ala His Val Asp Ala Leu Arg
        115                 120                 125

Thr His Leu Ala Pro Tyr Ser Asp Glu Leu Arg Gln Arg Leu Ala Ala
    130                 135                 140

Arg Leu Glu Ala Leu Lys Glu Asn Gly Gly Ala Arg Leu Ala Glu Tyr
145                 150                 155                 160

His Ala Lys Ala Thr Glu His Leu Ser Thr Leu Ser Glu Lys Ala Lys
                165                 170                 175
```

```
        Pro Ala Leu Glu Asp Leu Arg Gln Gly Leu Leu Pro Val Leu Glu Ser
                    180                 185                 190

Phe Lys Val Ser Phe Leu Ser Ala Leu Glu Glu Tyr Thr Lys Lys Leu
                    195                 200                 205

Asn Thr Gln
                    210

<210> SEQ ID NO 11
        <211> LENGTH: 278
        <212> TYPE: PRT
        <213> ORGANISM: Homo sapiens
        <220> FEATURE:
        <221> NAME/KEY: SITE
        <222> LOCATION: (1)..(278)
        <223> OTHER INFORMATION: MSP1E3D1

<400> SEQUENCE: 11

Met Gly His His His His His His Asp Tyr Asp Ile Pro Thr Thr
        1               5                   10                  15

Glu Asn Leu Tyr Phe Gln Gly Ser Thr Phe Ser Lys Leu Arg Glu Gln
                    20                  25                  30

Leu Gly Pro Val Thr Gln Glu Phe Trp Asp Asn Leu Glu Lys Glu Thr
                    35                  40                  45

Glu Gly Leu Arg Gln Glu Met Ser Lys Asp Leu Glu Glu Val Lys Ala
                50                  55                  60

Lys Val Gln Pro Tyr Leu Asp Asp Phe Gln Lys Lys Trp Gln Glu Glu
        65                  70                  75                  80

Met Glu Leu Tyr Arg Gln Lys Val Glu Pro Leu Arg Ala Glu Leu Gln
                        85                  90                  95

Glu Gly Ala Arg Gln Lys Leu His Glu Leu Gln Glu Lys Leu Ser Pro
                    100                 105                 110

Leu Gly Glu Glu Met Arg Asp Arg Ala Arg Ala His Val Asp Ala Leu
                    115                 120                 125

Arg Thr His Leu Ala Pro Tyr Leu Asp Asp Phe Gln Lys Lys Trp Gln
                    130                 135                 140

Glu Glu Met Glu Leu Tyr Arg Gln Lys Val Glu Pro Leu Arg Ala Glu
        145                 150                 155                 160

Leu Gln Glu Gly Ala Arg Gln Lys Leu His Glu Leu Gln Glu Lys Leu
                        165                 170                 175

Ser Pro Leu Gly Glu Glu Met Arg Asp Arg Ala Arg Ala His Val Asp
                    180                 185                 190

Ala Leu Arg Thr His Leu Ala Pro Tyr Ser Asp Glu Leu Arg Gln Arg
                    195                 200                 205

Leu Ala Ala Arg Leu Glu Ala Leu Lys Glu Asn Gly Gly Ala Arg Leu
                    210                 215                 220

Ala Glu Tyr His Ala Lys Ala Thr Glu His Leu Ser Thr Leu Ser Glu
        225                 230                 235                 240

Lys Ala Lys Pro Ala Leu Glu Asp Leu Arg Gln Gly Leu Leu Pro Val
                        245                 250                 255

Leu Glu Ser Phe Lys Val Ser Phe Leu Ser Ala Leu Glu Glu Tyr Thr
                    260                 265                 270

Lys Lys Leu Asn Thr Gln
                    275
```

METHOD FOR PRODUCING ERYTHROCYTE PROTEINS

CROSS REFERENCE TO RELATED APPLICATIONS

The present application is a national phase entry under 35 U.S.C. § 371 of International Application No. PCT/EP2016/074792, filed Oct. 14, 2016, which claims priority from French Patent Application No. 1559895 filed Oct. 16, 2015, all of which are hereby incorporated herein by reference.

INTRODUCTION

Blood groups are determined by a set of surface antigens that are grouped into systems based on genetic criteria. Today there are 35 blood group systems (ABO, Rhesus, Kell, Duffy, MNS, etc.) defining more than 300 erythrocyte antigens. While some have a broad tissue distribution, such as ABO, others, such as rhesus (Rh), are specific to red blood cells. Certain antigens carried by erythrocytes are highly immunogenic, in particular those of the Rh and Kell systems.

The Rhesus (Rh) system is the most complex blood group system, as it is the most polymorphic and the most immunogenic from a transfusion standpoint. The common Rh phenotype comprises the major antigen RH1 (D) encoded by the RHD gene, and the RH2 (C), RH3 (E), RH4 (c) and RH5 (e) antigens encoded by the RHCE gene. According to allelic forms, 8 classic haplotypes are distinguished.

The Rh system plays an important role in transfusion medicine. Indeed, its antigens can be, in conditions of blood group incompatibilities, at the origin of the development of alloantibodies in recipients or pregnant women, thereby causing hemolytic accidents and/or Hemolytic disease of the newborn (HDN). In RhD negative pregnant women, anti-D alloimmunization corresponds to the synthesis of anti-D IgG antibodies in response to the transplacental passage of fetal RhD positive red blood cells into the maternal circulation. In return, maternal anti-Ds traversing the placenta into the fetal circulation cause hemolysis and anemia in the RhD positive fetus.

Today, although the eventual development of anti-D antibodies in most situations of incompatibility can be mostly avoided by high-performance screening tests and effective prophylaxis in RHD-negative pregnant women, cases of alloimmunization remain. In particular, certain subjects with a D-positive phenotype may develop anti-D alloantibodies directed against one or more missing epitopes, defining "partial D" phenotypes, which can be distinguished by the presence or absence of one or more D epitopes located within the extracellular loops of the RHD protein (Cartron et al, 1996). The D antigen is therefore a complex antigen, as it is composed of a mosaic of epitopes, of which at least nine (epD1 to epD9) have been defined by means of a battery of monoclonal antibodies (Tippett et al 1996).

Currently, identification of plasma antibodies directed against Rh antigens requires the use of panels made of test red blood cells expressing different Rh phenotypes. Although most of these phenotypes are common, certain correspond to rare blood groups, the availability of which can be a significant problem, in some cases making it difficult to identify antibodies directed against these antigens. In addition, the use of panels involves a risk of infectious agents in the sample.

It is in a context of blood safety identification of anti-Rh alloantibodies present in the serum of patients that we propose to develop new tools for their rapid and effective characterization, that do not depend on the availability of rare bloods. As such, production of the RhD protein, and more generally of Rh protein, appears as an alternative to overcome these problems of detecting alloantibodies directed against antigens of low prevalence, and even of more common antigens.

Since the discovery of genes encoding the Rh proteins, the molecular basis of Rh phenotypes has been identified (Mouro-Chanteloup et al, 1993) and the expression of recombinant Rh proteins has been conducted in different heterologous systems. Furthermore, techniques for the synthesis of membrane proteins in vitro have also been described, such as the use of nanodiscs (WO2007/038755; WO2005/081743; WO2015/095854), to solubilize and stabilize membrane proteins. To enable proteins expressed in vitro to be synthesized in a functional conformation, the lipid composition of nanodiscs is essential. Certain nanodiscs, particularly commercial nanodiscs, do not allow a conformation preserving the structure and/or activity of all membrane proteins to be obtained (Bernhard Frank et al. (2015). In contrast to the synthesis of Rh non-erythrocyte proteins (RHCG) whose expression levels allowed, after extraction of the plasma membrane, a functional reconstitution in proteoliposomes (Mouro, Chanteloup et al, 2010), it has been difficult to obtain significant membrane expression of the RHCE and RHD proteins in conformations conserving epitopes recognized by antibodies. Due to their complex oligomeric organization, these proteins can be expressed only in the presence of the associated RHAG protein (Rh-associated Glycoprotein) (Cartron et al 1999, Mouro-Chanteloup et al, 2002) (Goossens et al., Plos one, 2013). However, the latter could be expressed only at 10,000 copies/cell (10% of its expression on red blood cells) in heterologous systems. These expression levels are not compatible with the use of recombinant Rh proteins as a tool to detect antibodies in the serum of patients, in particular for antibodies of low titer or low affinity.

There is therefore still a need for a system allowing the expression of erythrocyte proteins in a native configuration and at levels sufficient to enable diagnostic use.

DESCRIPTION

This invention relates to an erythrocyte protein production system that enables large quantities of these proteins to be obtained in their native state.

Although until now it has not been possible to produce erythrocyte proteins such as RhD, RHCE, RhAG and UTB, regardless of the system used, the inventors have shown that it is possible to obtain large amounts these erythrocyte proteins in a conformation allowing them to retain epitopes recognized by antibodies, when produced in vitro in the presence of detergents, liposomes or nanodiscs, preferably in the presence of nanodiscs with a lipid composition of the POPC type.

The method optimized by the inventors for the acellular production of erythrocyte proteins such as RhD, RHCE, RhAG, or UTB has allowed novel compositions comprising said proteins to be obtained in larger amounts than had been possible with the methods of the prior art. In a particularly surprising manner, said method for the acellular production of erythrocyte proteins such as RhD allowed the use of the associated protein RHAG (Rh-Associated Glycoprotein) to produce said protein RhD to be dispensed with, in contrast to the teaching of the prior art (Mouro-Chanteloup et al., Blood 2002, Goossens et al., Plos one, 2013).

This invention therefore relates to an acellular system for producing erythrocyte proteins such as RhD, RHCE, RhAG or UTB characterized by the presence of detergents or liposomes or nanodiscs.

"Erythrocyte protein" means herein a protein expressed in the cells of the erythrocyte line. "Erythrocyte line" refers herein to all cell types whose differentiation leads directly or indirectly to red blood cells, including red blood cells. The erythrocyte line in terms of the invention comprises, inter alia, proerythroblasts, basophilic erythroblasts, polychromatophilic erythroblasts, acidophilic erythroblasts, reticulocytes and red blood cells. Preferably, an erythrocyte protein in terms of the invention is a protein that is primarily expressed in the erythrocyte line.

The erythrocyte protein of the invention is in particular a membrane protein. Said protein may be an integral membrane protein or a protein associated with the membrane. Preferably, the erythrocyte protein of the invention is an integral membrane protein; more preferably, it is a polytopic protein; even more preferably, said polytopic protein carries blood group antigens.

Among the erythrocyte proteins that are particularly relevant to the present invention, mention may be made of the RhD, RHCE, RhAG and UTB proteins and variants thereof. Indeed, it is currently impossible to produce these proteins in native form in large quantities. The production of erythrocyte Rh proteins in cellular systems is possible, but with an extremely low yield that is totally insufficient for diagnostic use. Moreover, cellular production requires coexpression with RhAG for correct targeting of certain proteins (e.g. RhD and RHCE). However, the method developed by the inventors for the production of integral polytopic proteins of the red blood cell membrane bearing blood group antigens, that is to say in particular RhAG, RhD, RHCE and UTB, allowed novel compositions comprising said proteins to be obtained in larger amounts than is possible with the methods of the prior art.

"RhD protein" means a non-glycosylated membrane protein of 417 amino acids, having 12 transmembrane domains and intracytoplasmic N- and C-terminal ends. The D antigen is a collection of epitopes dependent on conformation all along the RhD protein. There are many monoclonal antibodies recognizing these conformational epitopes of the RhD protein. These antibodies allow, among others, to verify the proper folding of said RhD protein or to characterize variants thereof (Advent and Reid, 2000). Preferably, the RhD protein is a protein having the sequence represented by SEQ ID NO. 5 (NP_001121163). Even more preferably, the RhD protein is encoded by the RHD gene the sequence of which is represented by SEQ ID NO. 1 (NM_001127691).

"RHCE protein" means an unglycosylated membrane protein of 417 amino acids, having 12 transmembrane domains and intracytoplasmic N- and C-terminal ends. Preferably, the RHCE protein is a protein having the sequence represented by SEQ ID NO. 6 (NP_065231). Even more preferably, the RHCE protein is encoded by the RHCE gene of which the sequence is represented by SEQ ID NO. 2 (NM_020485). The RHCE gene has a very high homology with the RHD gene: these two genes have about 96% identity.

"RhAG protein" as understood within the meaning of the invention is a glycosylated membrane protein of 409 amino acids, having 12 transmembrane domains. This protein has ammonium transporter activity. Preferably, the RhAG protein is a protein having the sequence represented by SEQ ID NO. 7 (NP_000315). Even more preferably, the RhAG protein is encoded by the RHAG gene of which the sequence is represented by SEQ ID NO. 3 (NM_000324).

"UTB protein" refers herein to a urea transporter having 10 transmembrane domains and intracytoplasmic N- and C-terminal ends. The UTB protein carries the Kidd antigens.

Preferably, the UTB protein is a protein having the sequence represented by SEQ ID NO. 8 (NP_001 122060). Even more preferably, the UTB protein is encoded by the SLC14A1 gene of which the sequence is represented by SEQ ID NO. 3 (NM_001 12858 8).

Many phenotypic variants are known for each of these loci, and in particular for the RHD locus (see for example Advent and Reid, The Rh blood group System: a review Blood 95 (2): 375-387, 2000; The Blood Group Antigen FactsBook, 3rd Edition, Ed. Marion E. Reid, Christine Lomas-Francis, Martin L. Olsson, Academic Press, 2012, ISBN: 978-0-12-415849-8).

As used herein, a "variant" of a gene or of a given protein means a polynucleotide or a polypeptide of which the sequence has at least 95%, preferably 97%, more preferably 98%, even more preferably 99%, homology with the sequence of said gene or said protein, respectively. These variants may occur by at least four mechanisms: (1) chromosomal rearrangements; (2) point mutations resulting in one or more amino acid changes; (3) nonsense mutations and (4) nucleotide deletions leading to the occurrence of stop codons.

Chromosomal rearrangements affecting erythrocyte protein genes of the invention are well-known. For example, the RHCE and RHD genes that are highly homologous (over 96% identity) are arranged in tandem, which facilitates gene rearrangements between these genes and the emergence of "hybrid genes."

Moreover, the RHD and RHCE genes show a high degree of polymorphism. Similarly, there exists many variants for each of the RHAG and SLC14A1 genes. Numerous mutations in these genes have been described (see for example: The Blood Group Antigen FactsBook, 3rd Edition, Ed. Marion E. Reid, Christine Lomas-Francis, Martin L. Olsson, Academic Press, 2012, ISBN: 978-0-12-415849-8). Reference can also be made to the site "Blood Group Antigen Gene Mutation Database" www.ncbi.nlm.nib.gov, which compiles the different mutations found in each of these genes.

The method of the invention allows not only to produce each of the RhD, RHCE and UTB proteins, but also all variants of each of these proteins.

In certain embodiments, codon usage of the nucleotide sequence encoding the erythrocyte protein of interest is optimized for use in acellular systems derived from different organisms other than man (for example, bacteria such as *E. coli*). Here, the term "codon optimization" refers to a process by which a nucleotide sequence encoding a polypeptide of interest is modified to be optimized for expression in a particular organism without altering the amino acid sequence of said polypeptide. A "codon" is a sequence of three nucleotides translated into a particular amino acid in a cell. It is well-known that there are sixty-four possible combinations of sequences of three nucleotides, while there are only twenty natural amino acids. Thus, most amino acids are coded by several codons. Certain codons in a given species are often better translated than other codons encoding the same amino acid. In addition, the preferences of codon usage vary by species. Because of this, it was observed that the expression of a gene from one species may not be optimal when this gene is introduced into another species. The skilled person will readily understand that it is possible to overcome this problem by taking advantage of the degeneracy of the genetic code. Thus, a nucleotide sequence encoding a polypeptide of interest will be modified so that said sequence now contains codons which are effectively used in the species of interest, but without altering the sequence of the encoded polypeptide. It is possible to determine which codons are the most widely used in the organism of interest. This has already been done for many organisms, including organisms from which the most commonly used acellular systems are derived (*E. coli*, rabbit, wheat). The skilled person will thus be able to fully determine the codon usage for each organism of interest.

According to a particular embodiment, the acellular proteins of the invention are fused to a tag sequence in order to facilitate subsequent recovery or even purification. Such sequences are well-known to the skilled person. They include HA, FLAG, V5 and myc epitopes, as well as chitin binding protein (CBP), maltose binding protein (MBP), glutathione-S-transferase (GST) and the Strep tag. It is also possible to use a sequence of 6 histidines. These sequences can be added to the N-terminus or C-terminus of the protein of interest.

This invention therefore relates to a method for synthesizing an erythrocyte protein selected from RhD, RHCE, RhAG and UTB, or a variant thereof, said method comprising the steps of:
 a) contacting a nucleic acid encoding said protein or variant thereof with an acellular protein production system in the presence of at least one non-ionic detergent, liposomes or nanodiscs; and
 b) synthesis of said protein.

According to a preferred embodiment, this invention relates to a method of synthesizing an erythrocyte protein selected from RhD, RhCE, RhAG and UTB, or a variant thereof, said method comprising the steps of:
 a) contacting a nucleic acid encoding said protein or a homolog having at least 95% identity therewith with an acellular system for protein production, in the presence of at least one non-ionic detergent, liposomes or nanodiscs; and
 b) synthesis of said protein.

In terms of the invention "acellular system protein production" means a biochemical system for the synthesis of a protein in the absence of a cell. The acellular system for protein production in terms of the invention therefore contains all necessary elements for the production of proteins in the absence of a cell. In particular, this system comprises, inter alia, transcriptional and translational machinery from the cell.

These in vitro systems are particularly advantageous in that they permit the synthesis of cytotoxic membrane proteins or regulatory or unstable proteins, which cannot be expressed in living organisms, and therefore, in conventional in vivo systems. In particular, acellular systems are particularly suited to the expression of membrane proteins such as the erythrocyte proteins of the invention. Indeed, membrane proteins are very difficult to express in cells, the expression on the cell membrane requiring intracellular trafficking and proper targeting. Most of the techniques applicable to soluble proteins fail to cope with insoluble aggregates, particularly during the extraction and purification stages. In contrast, acellular systems are advantageous over conventional protein synthesis systems in that they offer the ability to change the reaction environment of the protein fairly simply, for example with the addition of reagents promoting correct folding. In fact, each reaction parameter (such as pH, redox potential, ionic strength, etc.) can be changed according to the target protein to be produced. In addition, in these systems, the resulting recombinant protein represents the major product of the reaction.

The template for acellular protein synthesis may be any type of polynucleotide, RNA or DNA. Preferably, the matrix used is a DNA molecule. In this case, the acellular system can convert the information contained in the DNA template into protein by coupling the transcription and translation reactions.

The coupled system, used in particular in *E. coli* systems, continuously generates mRNA from a DNA template comprising a recognizable promoter. In this system, an endogenous RNA polymerase can be used, but it is preferable to add an exogenous RNA polymerase, typically that of the T7 phage or the phage SP6, to the reaction mixture. The system can be used with any gene of interest. In particular, the DNA template of the invention comprises an expression cassette for expressing the erythrocyte protein of interest.

"Expression cassette" means herein a DNA fragment comprising a polynucleotide of interest, for example a polynucleotide encoding an erythrocyte protein of the invention, operably linked to one or more regulatory elements controlling the expression of gene sequences, such as, for example, promoter sequences and "enhancer" sequences.

A polynucleotide is "operably linked" to regulatory elements when these different nucleic acid sequences are associated on a single nucleic acid fragment so that the function of one is affected by the others. For example, a regulatory DNA sequence is "operatively linked" to a DNA sequence encoding an RNA or a protein if the two sequences are situated such that the regulatory DNA sequence affects expression of the coding DNA sequence (in other words, that the coding DNA sequence is under the transcriptional control of the promoter). The coding sequences can be operably linked to regulatory sequences both in a sense orientation and in an antisense orientation.

Preferably, the coding sequences of the invention are operably linked to regulatory sequences in the sense orientation.

"Regulatory sequences" or "regulatory elements" refer herein to polynucleotide sequences which are necessary to affect the expression and processing of coding sequences to which they are ligated. Such regulatory sequences notably comprise transcription termination sequences, promoter sequences and "enhancer" sequences; efficient RNA processing signals such as splicing and polyadenylation signals; sequences stabilizing cytoplasmic mRNA; sequences improving translation efficiency (for example, Kozak sequences); sequences that enhance protein stability; and, if necessary, sequences that enhance protein secretion.

Preferably, the regulatory sequences of the invention include promoter sequences, i.e., the gene encoding the erythrocyte protein of the invention is preferably operably linked to a promoter which allows expression of the corresponding mRNA. A gene encoding a protein erythrocyte is preferably operably linked to a promoter when it is located downstream from the latter, thereby forming an expression cassette.

"Promoter" as used herein means a nucleotide sequence, most often located upstream (5l)l of the coding sequence, which is recognized by RNA polymerase and other factors required for transcription, and as such controls the expression of said coding sequence. A "promoter" as used herein includes in particular minimal promoters, i.e., short DNA sequences composed of a TATA box and other sequences that make it possible to specify the transcription site start. A "promoter" in terms of the invention also comprises nucleotide sequences including a minimal promoter and regulatory elements capable of controlling the expression of a coding sequence. For example, the promoter sequences of the invention may contain regulatory sequences such as "enhancer" sequences that can influence the level of expression of a gene.

Advantageously, the promoters according to the invention are those operating with the RNA polymerase used in the acellular system of interest. For example, promoters recognized by SP6 and T7 phage RNA polymerases are widely known to the person skilled in the art. Thus, pIVEX vectors that carry promoters recognized by T7 RNA polymerase (Rogé and Betton, 2005) were used in the experimental section hereinafter. Vectors containing such promoters are also commercially available.

According to the invention, detergents, liposomes or nanodiscs are added to the reaction medium, either during protein synthesis, or preferably even before the start of protein synthesis. Up to a few milligrams per ml of this lipid is preferably added to the reaction medium, generally between 0.5 and 10 mg/ml.

"Detergent" as used herein means an amphipathic molecule containing both hydrophobic and hydrophilic groups. These molecules contain a polar hydrophilic group and a long hydrophobic carbon chain. The term "non-ionic detergent" means a molecule which contains a detergent in which the hydrophilic moiety is uncharged. The non-ionic detergents according to the invention comprise inter alia, alkyl polyglucosides, octaethylene glycol monododecyl ether (C12E8), detergents of the Brij family such as, for example, Brij 35 (C12E23 Polyoxyethyleneglycol dodecyl ether) or Brij 58 (C16E20 Polyoxyethyleneglycol dodecyl ether), Genapol, glucanids such as MEGA-8, -9, -10, octylglucoside, Pluronic F127, detergents of the Triton family such as Triton X-100 (C14H220(C2H40)n) or Triton X-114 (C24H4206), and detergents of the Tween family, in particular Tween 20 (polysorbate 20) and Tween 80 (Polysorbate 80). Preferably, the non-ionic detergent of the invention is selected from Brij 35 and Brij 58. More preferably, the non-ionic detergent of the invention is Brij 35. According to this preferred embodiment, the invention therefore relates to a method as described above, wherein the contacting according to step a) takes place in the presence of at least one non-ionic detergent selected from Brij 35 and Brij 58.

The most effective detergent concentrations for producing erythrocyte proteins according to the method of the invention vary from one detergent to another. They vary depending on the low critical micelle concentration of the detergent, i.e. the concentration from which micelles are formed. Nevertheless, these concentrations are typically comprised between 0.1 and 5%, more particularly between 0.1 and 1%. For example, Brij 35 and Brij 58 are typically used at 0.5%. Depending on whether a given detergent is solid or liquid, % refers respectively to a w/v % or v/v % ratio.

"Liposome" as used herein means an artificial vesicle formed by concentric lipid bilayers, between which aqueous compartments are trapped. Liposomes can be made of any suitable lipid, including, but not limited to, polar lipids such as phospholipids, such as phosphoglycerides, such as phosphatidylethanolamine, phophatidylcholine, phosphatidylserine, cardiolipin, or combinations thereof. Other lipid compounds can also be incorporated into liposomes, such as triacylglycerols, waxes, sphingolipids and sterols and their fatty acid esters, or combinations thereof.

The lipid vesicles correspond to lipid bilayers in the form of spheres of a diameter of approximately 100 nm, prepared using protocols known to the person skilled in the art.

These lipid vesicles may be treated with detergents prior to introduction into the reaction medium. According to a first embodiment, the lipid vesicles used are of natural origin, preferably from soy or eggs. Such lipids are commercially available from Avanti Polar Lipids resold by Coger in France. Alternatively, the lipid vesicles can be liposomes of synthetic origin, i.e. produced from synthetic lipids.

According to a preferred embodiment and in particular in the case of synthetic lipids, the liposomes used in the context of the invention are carriers of polyethylene glycol (PEG) molecules or PEG derivatives (functionalized PEG) such as N-carbonyl-methoxypolyethylene glycol 2000.

The term "nanodisc" as used herein refers to at least one lipid bilayer stabilized by a protein framework. Preferably, said framework surrounds the lipid bilayer so as to form a discoid structure.

Lipid" as used herein means any natural liposoluble molecule (i.e. lipophilic). Lipids are a heterogeneous group of compounds with many essential biological functions. These compounds function as structural components of cell membranes, as well as energy storage sources or as intermediate molecules in signaling pathways. Lipids can be defined as small hydrophobic or amphiphilic molecules that originate entirely or in part from ketoacyl or isoprene groups. For an overview of all lipid classes, reference may be made advantageously to "Lipid Metabolites and Pathways Strategy (LIPID MAPS) System classification" (National Institute of General Medical Sciences, Bethesda, Md.). Lipids may form micelles, monolayer membranes, and bilayer membranes. Lipids may self-assemble in combination if necessary with other components to form nanodiscs. Lipids in terms of the invention include fats, waxes, phospholipids, sphingolipids (such as sphingomyelin), sterols (such as cholesterol), cerebrosides and compounds which are derived from each of these lipid groups. The lipids used in the nanodiscs in terms of the invention are preferably phospholipids. A "phospholipid" in terms of the invention is a lipid containing a phosphoric acid group as a mono or di-ester. Phospholipids which may be used in the nanodiscs of the invention comprise synthetic, natural, saturated, unsaturated phospholipids, their derivatives (for example, acyl, diether and lyso) and any combination of phospholipids of different classes or of the same class that can promote good insertion and conformation of the expressed protein and, by the same, its recognition by ligands or antibodies. Phospholipids comprise inter alia phosphatidylcholine, phosphatidic acid, phosphatidylethanolamine, phosphatidylglycerol, phosphatidylserine, phosphatidylinositol, phosphatidylinositolphosphate, cardiolipin, and derivatives thereof. In a preferred embodiment, phospholipids comprise the dioleoyl, dimyristoyl, palmitoyl oleoyl-glycero-phosphocholines (DOPC, DMPC, POPC), the palmitoyl-oleoyl, dimyristoyl and dioleoyl phosphoglycerols (POPG, DMPG and DOPG). In an even more preferred embodiment, phospholipids comprise the dioleoyl, dimyristoyl, palmitoyloleoyl-glycero phosphocholines (DOPC, DMPC, POPC). According to a particularly advantageous embodiment, the phospholipids of the invention are combined with sodium cholate. According to this embodiment, removing this salt, for example by dialysis, enables nanodiscs to be obtained from phospholipids and the protein framework of the invention.

The term "protein framework" as used herein includes any protein capable of assembling with an amphipathic lipid in an aqueous environment and organizing said amphipathic lipid in a bilayer. Preferably, the protein framework of the present invention must be amphipathic, with one part of its structure more or less hydrophilic and facing the aqueous solvent and the other part more or less hydrophobic and facing the center of the hydrophobic bilayer that is thus stabilized. The term "protein framework" thus includes, but is not limited to, apolipoproteins, lipophorines, derivatives thereof (such as, for example, truncated and tandemly arranged sequences) and their fragments (i.e. of the peptides) such as apolipoprotein E4, the 22K fragment, liphorine III, apolipoprotein A1 and similar molecules. The protein framework may also be constituted by artificial amphipathic peptides designed specifically for this purpose. In some particular embodiments, these peptides are amphipathic helicoidal peptides that mimic apolipoprotein alpha helices which are oriented perpendicular to the fatty acid chains of amphipathic lipids, particularly those of phospholipids. Such peptides are described in parent application WO 2008/141230 A1.

Preferably, the protein framework of nanodiscs of the invention is constituted by the MSP1 protein, or a derivative thereof. MSP1 is a truncated form of the A1 apolipoprotein, which has the same amphipathic helicoidal structure as the complete protein. The MSP1 protein has the sequence:

(SEQ ID NO. 9)
GLKLLSNWDSVTSTFSKLREQLGPVTQEFWDNLEKETEGLRQEMSKDLEE

VKAKVQPYLDDFQKKWQEEMELYRQKVEPLRAELQEGARQKLHELQEKLS

PLGEEMRDRARAHVDALRTHLAPYSDELRQRLAARLEALKENGGARLAEY

HAKATEHLSTLSEKAKPALEDLRQGLLPVLESFKVSFLSALEEYTKKLNT

Q.

Derivatives of this protein have been constructed (see for example, Grinkova et al., 2010, WO 02/40501, WO 2005/081743, U.S. Pat. No. 7,083,958 B2). Some of these derivatives comprise sequences permitting easy purification of the protein and nanodiscs into which they are incorporated. As such a tag sequence may be added to the protein. Such sequences are well-known to those skilled in the art. They comprise the HA, FLAG, V5 or myc epitope, as well as chitin binding protein (CBP), maltose binding protein (MBP), glutathione-S-transferase (GST) and the Strep tag, or a sequence of 6 histidines. For example, a sequence of 6 histidines may be fused to the N-terminal of the MSP1 protein. Certain derivatives of MSP1 contain a site recognized by TEV protease, which has been modified to cause a complete and specific cleavage. The MSP1 derivatives may also comprise an additional truncation Δ (1-11) at the N-terminal of MSP1. This truncation gives more stable discs, the entirety of the first helix not being required for interaction with lipids. The M1PD1 protein (SEQ ID NO. 10) thus comprises the truncation Δ (1-11) fused to a His6 sequence and a TEV site at the N-terminal. The MSP1D1 protein generates nanodiscs of a diameter of approximately 9.7 nm, which typically contain between 120 and 160 molecules of lipid and two MSPs per nanodisc. Another derivative commonly used by those skilled in the art is the protein MSP1E3D1 (SEQ ID NO. 11) which comprises an insertion of three additional helices (4, 5 and 6) between helices 3 and 4 of the MSP1D1 protein. This protein thus comprises a duplication of helices 4, 5 and 6 of the MSP1D1 protein. As a result, it generates nanodiscs which have a larger size than those obtained with the MSP1D1 protein: about 12.9 nm. These two derivatives, MSP1D1 and MSP1E3D1, are most commonly used to generate nanodiscs. They are also both commercially available (from Sigma-Aldrich or Cube Biotech among others). Very preferably, the MSP protein of the invention is a protein having a sequence selected from SEQ ID NO. 9, 10 or 11.

According to this preferred embodiment, the invention relates to a method as described above, wherein the contacting according to step a) is carried out in the presence of nanodiscs comprising a MSP protein chosen from the proteins of SEQ ID NO. 9, 10 or 11.

The invention therefore relates to a method as described above, wherein the contacting according to step a) takes place in the presence of at least one non-ionic detergent selected from Brij 35 or Brij 58 or nanodiscs comprising a MSP protein selected from the proteins of SEQ ID NO. 9, 10 or 11.

The inventors have shown that the use of nanodiscs enables erythrocytic proteins of the invention to be obtained in soluble form and in large quantities. In particular, they have shown that it is important to use an adequate nanodisc concentration to optimize production. In this regard, a nanodisc concentration of less than 80 µM is particularly suitable for obtaining a large amount of protein in a soluble state. For example, nanodisc concentrations of 20 µM, 40 µM or 60 µM enable yields that are at least as good as those obtained in the presence of detergent to be obtained.

The methods for generating nanodiscs with lipids, preferably phospholipids, and a protein that can form a framework are well-known to those skilled in the art (see for example Denisov et al., 2004). They will thus not be detailed here, but note that, in addition, many companies offer nanodiscs (for example, Cube Biotech, Sigma Aldrich, Nanodiscs Inc.).

The acellular system has, as a basic principle, the use of the transcriptional and translational machinery of an organism to produce a specific recombinant protein from exogenous genetic information. The organisms from which the machinery is extracted are many and varied, and are derived from prokaryotic and eukaryotic organisms.

Such systems have been well-known to those skilled in the art for several decades (for a review, see for example: Carlson et al, 2012). Many methods are available to synthesize proteins in acellular systems (see for example Cellfree Protein Synthesis: Methods and protocols, edited by Alexander S. Spirin and James R. Swartz 2008. Wiley-VCH, Weinheim, Germany). It is also possible to use kits offered by various companies: Qiagen, Ambion, Promega, Invitrogen, Thermo Scientific, Roche Diagnostics, CellFree Science & Co, etc.

Preferably, the acellular systems for producing proteins of the invention comprise cell extracts. Although any organism can be used as source of cell extracts, it is preferable to use extracts of *Escherichia coli*, rabbit reticulocyte, wheat germ or insect cells. *E. coli* extracts are particularly advantageous. First, those skilled in the art already have extensive experience with this system, which is by far the most popular. These extracts may be prepared easily and at low cost. They may provide very high yield at a lower energy cost than other systems. This system is readily available commercially, as many companies are currently marketing protein acellular expression kits using extracts of *E. coli*: Qiagen, Promega, Invitrogen, Thermo Scientific, Roche Diagnostics, etc.

There are two ways to perform the acellular reaction. In discontinuous reactions, also called batch reactions, transcription and translation are performed in a reaction volume containing all necessary components. For various reasons, such as the rapid depletion of energy supply, the deterioration of components such as nucleotides and decreasing concentrations of $Mg^{2+}$ free ions, the reaction in the batch system typically reaches a plateau after about 1-2 hours. The use of an optimized in vitro batch expression system generally produces up to 500 µg protein/ml, although higher amounts may sometimes be achieved at the cost of additional optimization.

In a dialysis mode, the acellular transcription/translation reaction is performed in a small reaction chamber which is separated by a dialysis membrane (usually 10 to 15 kDa cutoff) from a reservoir approximately 10 to 20 times larger containing low molecular weight reagents.

In the first of the systems in dialysis mode, the continuous flow acellular production system or Continuous Flow Cell Free (CFCF), the reaction medium is sequestered by an ultrafiltration membrane and is continuously fed by a pump. This membrane allows the protein of interest to pass into the buffer compartment and be recovered while continuing to feed the reaction and thus perform reactions for several tens of hours.

In an acellular production system with continuous exchange (Continuous Exchange Cell Free or CECF), the reaction chamber containing the cell lysate and genetic information is separated from a nutrition compartment containing cofactors, amino acids, buffers and other components by a dialysis membrane. The dialysis membrane allows the outflow of waste molecules, but allows entry of components that enable the reaction to proceed due to the concentration gradient resulting from synthesis activity. This configuration makes it possible to significantly increase the reaction time and the levels of protein produced. Yields of up to 5 mg/ml in the reaction volume were reported for the *E. coli* system of with this method, both with commercial (RTS, Roche Applied Science) and homemade systems.

The acellular system of the invention is a system in batch or dialysis mode. Preferably, this system is a dialysis mode system. More preferably, this system is an acellular production system with continuous exchange.

The advantage of the acellular system is that it provides the ability to precisely control reaction parameters. In addition to extracts, acellular systems for protein production include many elements of which the concentration may be critical for reaction efficiency.

Divalent $Mg^{2+}$ ions are essential in many biological reactions. Here, the inventors have shown that a magnesium concentration comprised between 14 and 22 mM, preferably between 16 and 20 mM makes it possible to obtain significant yields of erythrocyte proteins. The acellular protein production system according to the invention thus comprises a magnesium concentration of between 14 and 22 mM, preferably between 16 and 20 mM.

Other salts, particularly those that are biologically relevant, such as manganese, may also be added. Potassium is generally present at a concentration of at least about 50 mM, and not more than about 250 mM. Ammonium may be present, usually at a concentration of less than 200 mM, generally at a concentration of less than about 100 mM. Usually, the reaction is maintained in the pH range of about 5 to 10 and a temperature of about 20°-50° C.; more generally in the pH range of about 6-9 and a temperature of about 25°-40° C. Advantageously, the reaction is carried out at pH=7.5. Moreover, a temperature of 20° C. is particularly advantageous for this reaction. These ranges may be extended for specific conditions of interest.

In contrast, there is no need to add exogenous cofactors for activation of oxidative phosphorylation. Compounds such as nicotinamide adenine dinucleotide, (NADH), $NAD^+$, or acetyl-coenzyme A may be used to supplement protein synthesis yields but are not required. Addition of oxalic acid, a metabolic inhibitor of phosphoenolpyruvate synthetase (Pps), may be beneficial in increasing protein yields, but is not necessary.

The erythrocyte proteins of the invention are membrane proteins. Thus, it is important that the membrane proteins produced in the acellular system be correctly folded and functional. In particular, it is important to avoid the formation of aggregates. In this regard, the inventors have shown that a reaction time comprised between 2 and 24 hours, preferably between 6 and 12 hours, more preferably about 8 hours, makes it possible to maximize yield while avoiding aggregates.

According to a particular embodiment, the method of the invention comprises a step of recovering the produced protein. This step may be facilitated by the use of a tag sequence. According to a particular embodiment, this sequence is fused to the erythrocyte protein of interest. It should be noted that when the erythrocyte protein of the invention is produced in the presence of nanodiscs, it may be advantageous to fuse the protein comprising the nanodiscs with a tag sequence and to use it to recover the protein of the invention.

The isolation (or purification) of the erythrocyte protein of the invention can be achieved by any means known to the person skilled in the art. Examples include differential precipitation or ultracentrifugation. It may also be advantageous to purify the fragments of interest by ion exchange chromatography, affinity chromatography, molecular sieving, or isoelectric focusing. All of these techniques are described in Voet D and Voet J G, Techniques of Protein and Nucleic Acid Purification, Chapter 6, Biochemistry, 2nd edition. Preferably, the protein of interest can be recovered by immunoprecipitation using for example antibodies directed against this protein. Alternatively, the protein of interest can, if necessary, be isolated by affinity chromatography using the tag sequence.

It may be particularly useful in certain applications to couple the erythrocyte protein of interest to a solid support, for example, to detect antibodies directed against alloantigens carried by the protein in the serum of a subject. Coupling of said protein may be direct or indirect. The coupling of the protein is direct when the protein interacts with the solid support without the intermediary of another protein. This is the case for example when the coupling is achieved via antibodies directed against the protein of interest. This is also the case when the protein of interest is itself fused to a tag sequence. Indirect coupling in the context of the invention means a coupling mediated by another protein, for example, by the MSP or by a fusion between a MSP protein and a tag sequence. In this case, said other protein is coupled to the solid support and the protein of interest is itself coupled thereto only to the extent with which it interacts with said other protein. For example, the protein of interest is indirectly coupled to a solid support when expressed in nanodiscs whose MSP protein is bound to said solid support. This coupling mode may be advantageous in not disturbing the three-dimensional organization of the protein of interest.

According to this particular embodiment, the method of the invention comprises an additional step of fixing the erythrocyte protein, or variant thereof, and/or the MSP protein to a solid support. Advantageously, a compound which specifically interacts with the erythrocyte protein, or variant thereof, and/or the MSP protein is grafted on said solid support. Said compound is, for example, an antibody directed against the erythrocyte protein of interest or against the MSP protein. Preferably, this compound is recognized by the tag sequence of the erythrocyte protein, or variant thereof, and/or the MSP protein. This compound may be an antibody recognizing a specific epitope, such as HA, FLAG, V5 or myc. It may also be a sugar (chitin or maltose, for example) or a metabolite (such as glutathione) which is bound by a protein (CBP, MBP and GST, respectively). Said compound may also be a peptide, optionally modified by genetic engineering, which is recognized and bound by a specific peptide sequence: as such, the Strep-Tactin peptide is derived from streptavidin by genetic modification and is bound by a specific sequence, the Strep-tag. Finally, this compound may be a divalent ion such as $Ni^{2+}$, which is bound by a sequence of 6 histidines. The methods for coupling these compounds to solid supports are well-known to those skilled in the art. They are therefore not covered in detail here.

The solid carrier which can be used in the present invention is not limited in any way as long as it is a solid support or composed of an insoluble material (for example, a material that can be separated from a reaction mixture by filtration, precipitation, magnetic separation or any other suitable technique).

The materials constituting said solid support comprise, but are not limited to, cellulose, Teflon☐, nitrocellulose, agarose, dextran, chitosan, polystyrene, polyacrylamide, polyester, polycarbonate, polyamide, polypropylene, nylon, polydivinylidene difluoride, latex, silica, glass, fiberglass, gold, platinum, silver, copper, iron, stainless steel, ferrite, wafer silicon, polyethylene, polyethyleneimine, polylactic acid, resins, polysaccharides, proteins (e.g. albumin), carbon, and combinations thereof.

The solid support can have any shape, including but not limited to that of bead, magnetic bead, thin film, micro tube, filter, plate, microplate, carbon nanotube, sensor chip, etc. Flat solid supports such as films or thin plates may also comprise wells, canals, filter drains or other, as is known in the art. In fact, the solid support may be any surface on which the compound recognized by the tag sequence can bind. The solid support according to the invention comprises, inter alia, microtiter plates, beads, disks, chips, slides, and any other suitable support.

In one embodiment of this invention, the solid support consists of magnetic beads having a spherical diameter comprised between about 25 nm and about 1 mm. In a preferred embodiment, the magnetic beads have a diameter comprised between about 50 nm and about 10 µm. The size of the magnetic beads can be selected according to the intended use.

According to another embodiment of the present invention, the solid support comprises beads composed of highly crosslinked spherical agarose (for example, sepharose). Preferably, said beads have a diameter comprised between about 24 µm and about 165 µm. In a more preferred embodiment, said beads have a diameter between about 24 µm and about 44 µm. The size of these highly crosslinked spherical agarose beads can be selected according to the intended use.

Solid supports having a hydrophobic surface comprise inter alia polystyrene latex beads, such as those commercially available from Polysciences, Warrington, Pa. or Spherotech, Liberville, Ill.

Examples of silica ($SiO_2$) treated or silica ($SiO_2$) based solid support comprising superparamagnetic silica beads that are available from Polysciences, Warrington, Pa. It is also possible to use M-280 commercially available from Dynal Biotech, etc.

Magnetic beads having a hydrophilic surface may be used in the method of this invention. Examples of these magnetic beads include beads commercially available under the name Biomag® carboxyl from Polysciences, Warrington, Pa. or MC02N beads name/2928 from Bangs Laboratory, Inc., Fishers, Ind. It is also possible to use M-270 commercially available from Dynal Biotech, etc.

According to another aspect, the invention relates to an erythrocyte protein expressed in a nanodisc, a liposome or a non-ionic detergent, or a homolog having at least 95% identity therewith, wherein said protein or variant being obtainable by the method above.

According to another aspect, the invention relates to an erythrocyte protein selected from RhD, RhCE, RhAG and UTB, or a variant thereof, wherein said protein or variant is capable of being obtained by the method above, and is coupled to a solid support. Advantageously, the erythrocyte protein according to the invention is selected from RhD, RhCE, RhAG and UTB, or a homolog having at least 95% identity therewith, wherein said protein or homolog is capable of being obtained by the method according to the invention, and is coupled to a solid support. The erythrocyte protein thus obtained is properly folded, in contrast to the prior art extracting proteins from red blood cells without retaining conformation. Indeed, the inventors have shown that the RhD protein produced by the method of the invention is recognized by conformational antibodies usually used to characterize the native endogenous protein. Advantageously, the erythrocyte protein obtained by the method of the invention is functional.

According to yet another aspect, the invention relates to a composition comprising an erythrocyte protein selected from RhD, RhCE, RhAG and UTB, or a variant thereof. Preferably, the concentration of the protein in said composition is greater than 0.01 mg/ml, more preferably greater than 0.1 mg/ml, even more preferably greater than 0.5 mg/ml and still more preferably greater than 1 mg/ml.

The use of liposomes or nanodiscs in the process of the invention generates particles, proteoliposomes or nanodiscs of lipids and proteins, which include both the erythrocyte protein of interest and lipids. The invention thus relates to, in another aspect, a composition comprising an erythrocyte protein selected from RhD, RhCE, RhAG and UTB, or a variant thereof, and one or more lipids. Preferably, the concentration of the protein in said composition is greater than 0.01 mg/ml, more preferably greater than 0.1 mg/ml, even more preferably greater than 0.5 mg/ml and still more preferably greater than 1 mg/ml.

According to yet another aspect, the invention relates to a composition comprising an erythrocyte protein selected from RhD, RhCE, RhAG and UTB, or a variant thereof, and a MSP protein selected from proteins of SEQ ID NO. 9, 10 or 11. Such a composition is in particular obtained when nanodiscs are used in the method of the invention. Preferably, the composition of the invention also includes lipids. Preferably, the concentration of the erythrocyte protein contained in such a composition is greater than 0.01 mg/ml, more preferably greater than 0.1 mg/ml, even more preferably greater than 0.5 mg/ml and still more preferably greater than 1 mg/ml.

According to yet another aspect, the invention relates to an erythrocyte protein selected from RhD, RhCE, RhAG and UTB, or a variant thereof, wherein said protein is coupled to a solid support. The coupling of said protein may be direct or indirect, as explained above.

The proteins of the invention are particularly important because they can be simply used in a test for detecting anti-erythrocyte alloantibodies. These are antibodies directed against antigens present on the surface of erythrocytes and that can induce hemolysis thereof. Anti-erythrocyte alloantibodies are produced against foreign erythrocyte antigens. The immunization takes place for example through a blood transfusion, during pregnancy, or at birth. If such IgG antibodies cross the placental barrier, they can induce accelerated destruction of a child erythrocytes or a blockage of fetal erythropoiesis.

According to this new aspect of the invention, the invention relates to the use of an erythrocyte protein or a composition comprising an erythrocyte protein in an alloantibody detection test.

The presence of such alloantibodies in a biological sample of a subject notably comprises contacting said sample with an erythrocyte protein or a composition comprising an erythrocyte protein as described above, followed by the detection, if appropriate, of the interaction between the erythrocyte protein and the antibodies directed against it.

"Subject" as used herein means a mammal, preferably a person, for example, a pregnant woman or a transfused patient. As used herein the term "biological sample" or "sample" refers to a whole organism or a subset of its tissues, cells or component parts. Furthermore "biological sample" refers to a homogenate, lysate or extract prepared from a whole organism or a subset of its tissues, cells or components, or a fraction or portion thereof. Preferably, a "biological sample" according to the invention is any tissue that may contain alloantibodies. "Biological sample", as used herein means for example humoral samples such as blood, bone marrow fluid, and lymphatic fluid and solid samples such as lymph nodes, blood vessels, bone marrow, brain, spleen and skin. More preferably, the biological sample of the invention is a sample of blood, plasma, or bone marrow.

The interaction between the erythrocyte protein of interest and the corresponding alloantibodies is detected by any means known to the person skilled in the art. They can in particular use well-known technologies such as immunoprecipitation, immunohistology, western blotting, dot blot, ELISA or ELISPOT, protein arrays, antibody microarrays or tissue chips coupled to immunohistochemistry. Other techniques that can be used comprise FRET or BRET techniques, methods of microscopy or histochemistry, including confocal microscopy and electron microscopy methods based on the use of one or more excitation wavelengths and an optical method adapted as an electrochemical method (voltametry and amperometry techniques), atomic force microscopy, and radio frequency methods, such as multipolar resonance spectroscopy, confocal and non-confocal, fluorescence detection, luminescence, chemiluminescence, absorbance, reflectance, transmittance, and birefringence or refractive index (for example, by surface plasmon resonance, by ellipsometry, by the resonant mirror method, etc.), flow cytometry, radioisotope or magnetic resonance imaging, polyacrylamide gel electrophoresis (SDS-PAGE analysis); HPLC-Mass spectrometry, liquid chromatography/mass spectrometry/mass spectrometry (LC-MS/MS). All of these techniques are well-known to the person skilled in the art and it is not necessary to detail them here.

The invention shall be described more precisely using the examples below.

FIGURE LEGENDS

FIG. 1. Detection of RHD protein by Western blotting. The total proteins of different syntheses were separated into soluble fraction and insoluble fraction by centrifugation, the RHD protein was revealed by the LOR-15C9 antibody and an anti-human secondary antibody conjugated with HRP ($1/1000$). The molecular weight markers (kDa) are indicated on the left and right.

Figure 2:
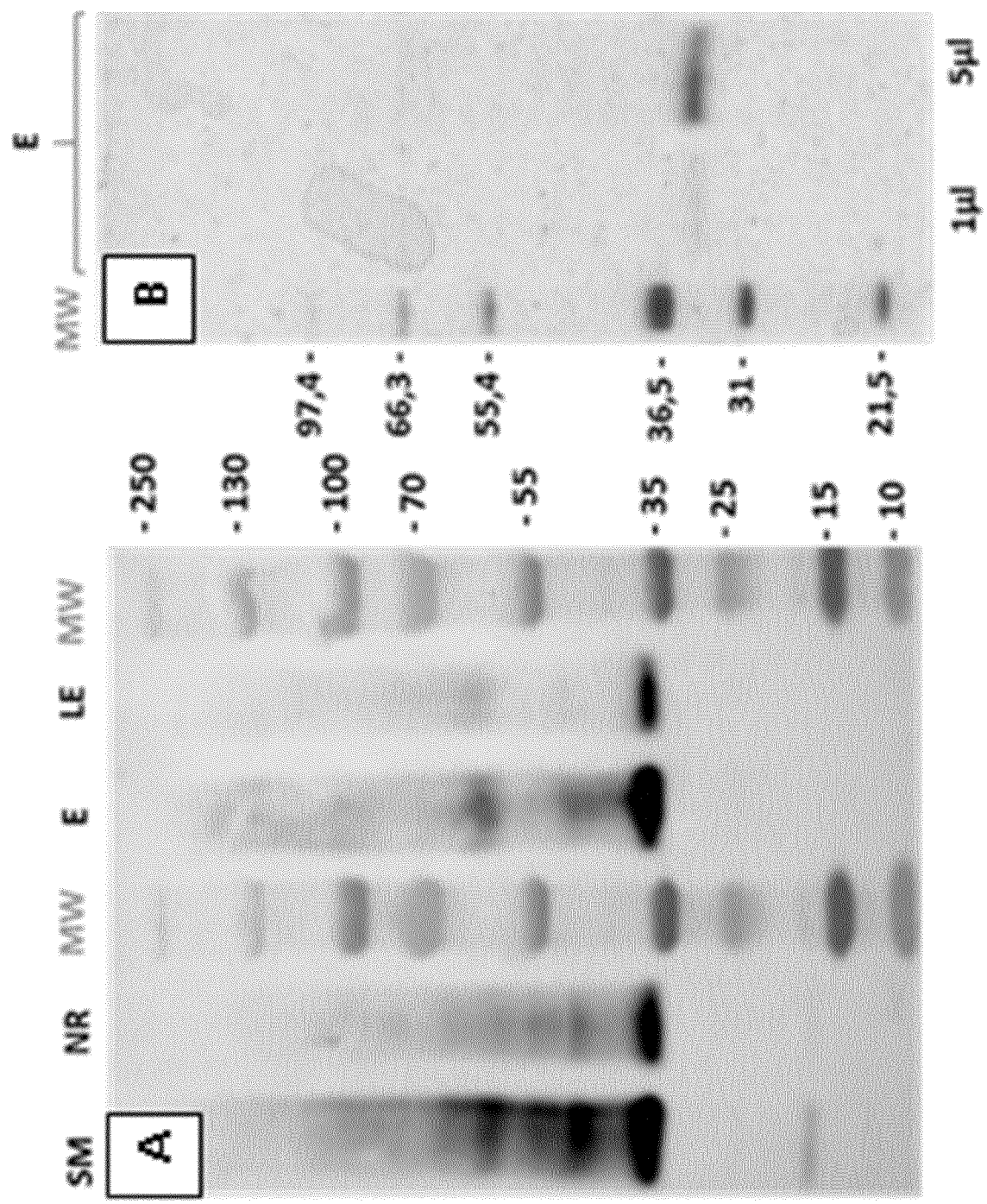

FIG. 2. Purification on Agarose HA of the protein produced in the presence of Brij 35 0.5%. Western blot analysis of purification steps using an anti-HA antibody ($1/2000$) (A) and analysis of the eluate by staining with silver nitrate (B). SM fraction is the in vitro synthesis product of the RHD protein, NR: fraction not retained by the resin, E: Eluate LE: elution wash, and MW: molecular weight marker (kDa).

Figure 3:
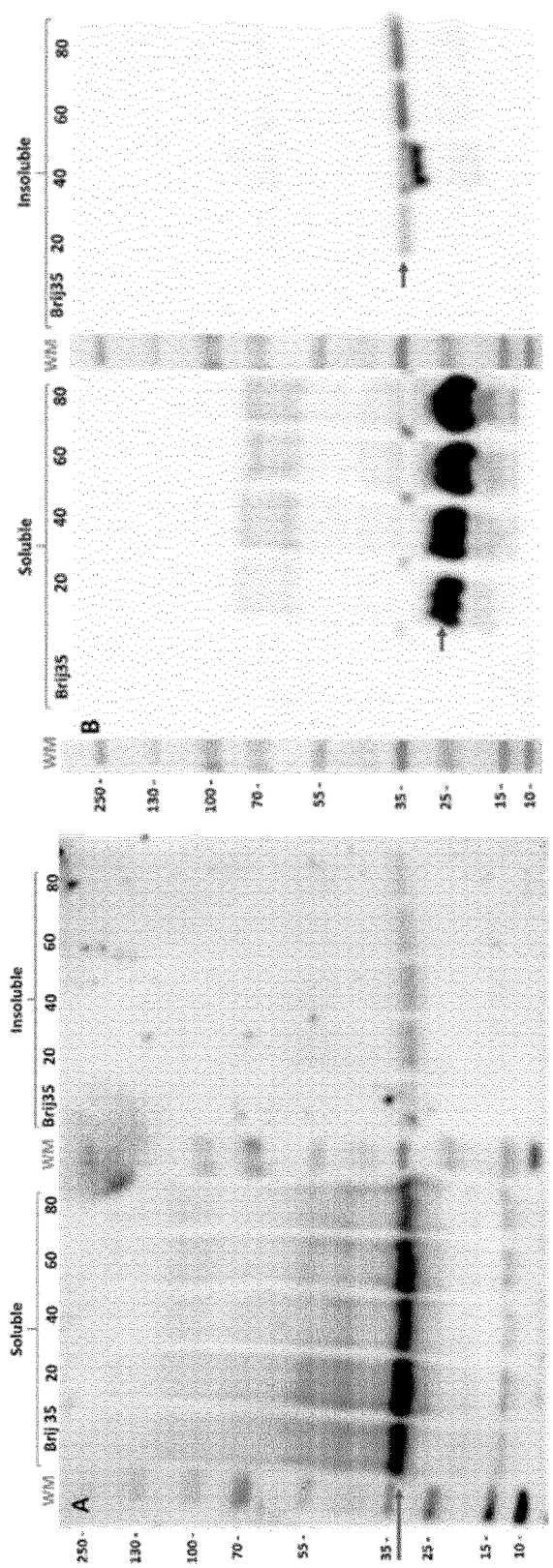

FIG. 3. Detection of RHD and MSP protein by Western blotting. Analysis of RHD protein synthesis products in the presence of nanodiscs or Brij 35. (A) RHD protein was revealed by LOR-15C9 antibody and an anti-human secondary antibody conjugated with HRP ($1/1000$). (B) The MSP protein was revealed by an anti-His antibody conjugated with HRP ($1/10,000$). MW is the molecular weight marker (kDa).

Figure 4:
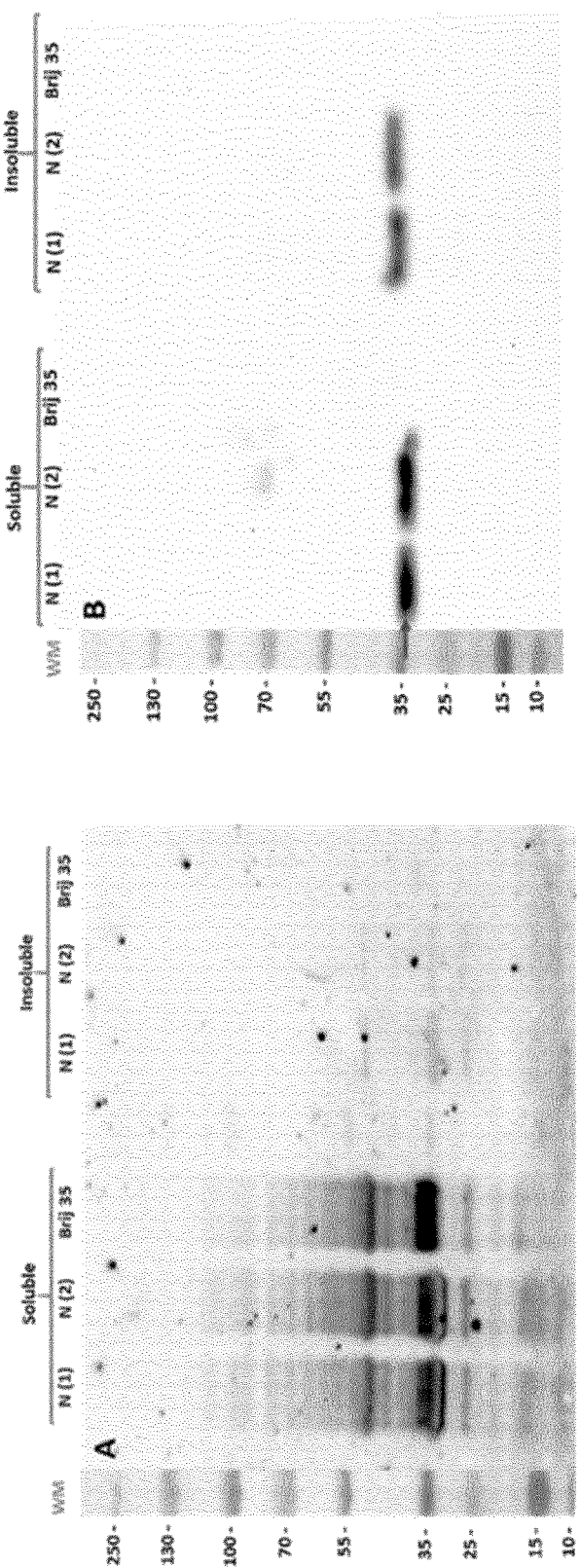

FIG. 4. Detection of RHD and MSP proteins by Western blotting. Analysis of soluble and insoluble fractions of productions of the RHD protein in the presence of 50 µM nanodiscs (N1, N2) or in the presence of 0.5% Brij 35. (A) RHD protein was revealed by LOR-15C9 antibody, and an anti-human secondary antibody conjugated with HRP ($1/800$). (B) MSP protein of the nanodiscs was revealed by an anti-His antibody conjugated with HRP ($1/10,000$). MW is the molecular weight marker (kDa).

Figure 5:
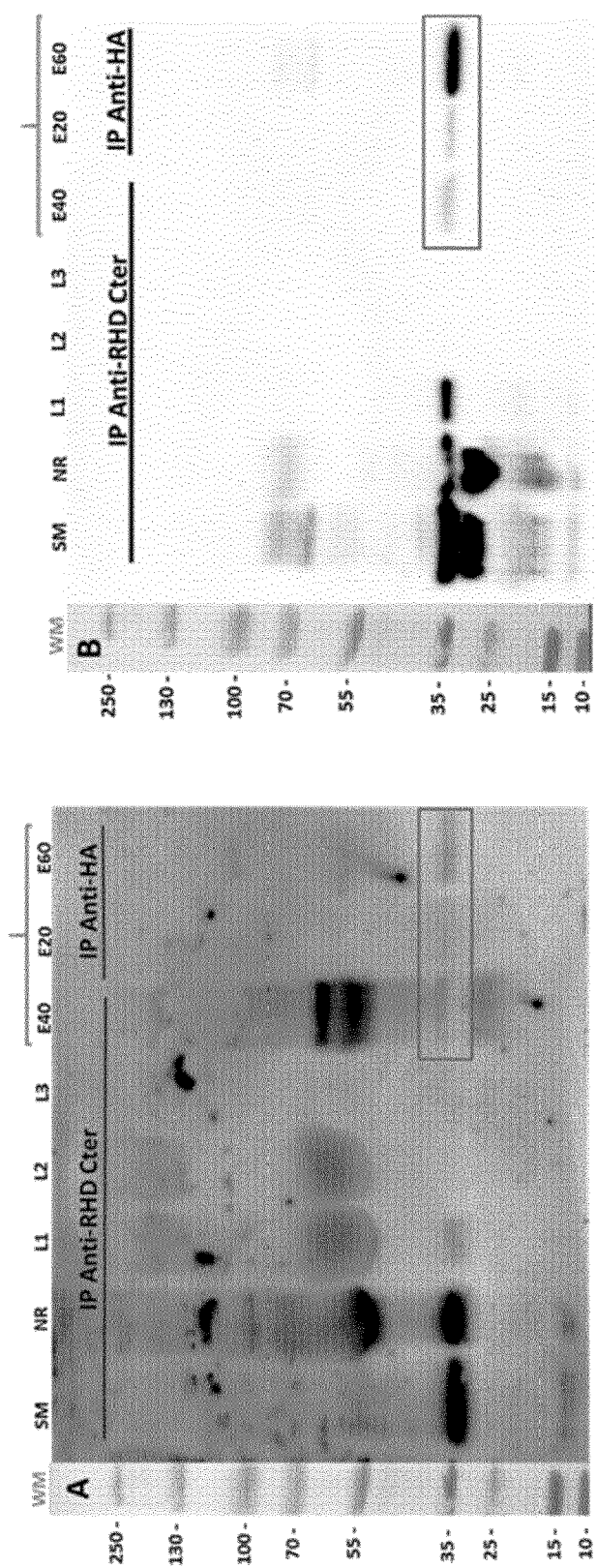

FIG. 5. Detection of RHD and MSP proteins by Western blotting. Analysis of the different purification steps of the RHD protein produced in the presence of 40 µM of nanodiscs (IP Anti-RHD Cter) and comparison with elution fractions of purified RHD proteins produced in the presence of 20 and 60 µM (IP Anti-HA). (A) RHD protein revealed by LOR-15C9 antibody, and an anti-human secondary antibody conjugated with HRP ($1/800$) (B) MSP protein of nanodiscs was revealed by an anti-His antibody conjugated with HRP ($1/10,000$). SM fraction is the in vitro synthesis product of the RHD protein, NR: fraction not retained by the resin, L1, L2, L3, fractions of the various washes, E 20/40/60: elution fractions, MW, molecular weight marker (kDa).

Figure 6:
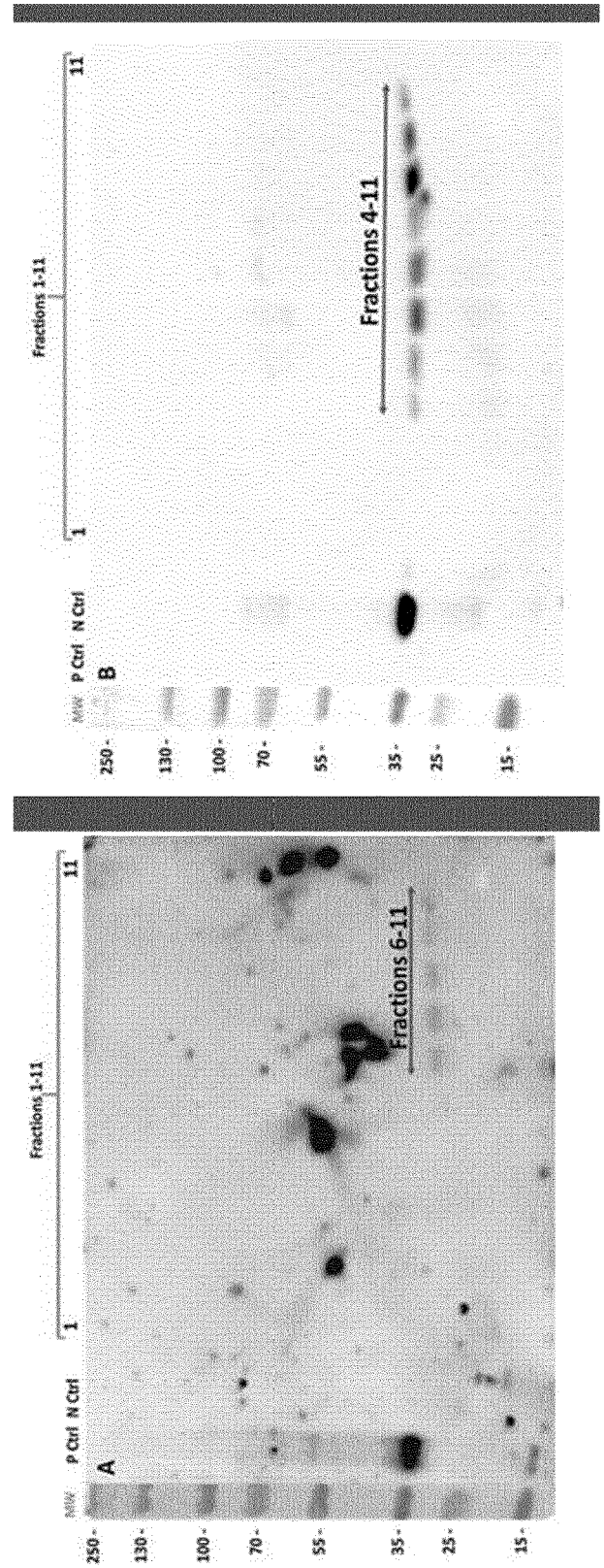

FIG. 6. Detection of RHD and MSP proteins by Western blotting. Analysis of fractions 1-11 of the sucrose gradient (A) RHD protein was revealed by LOR-15C9 antibody, and an anti-human secondary antibody conjugated with HRP ($1/800$). (B) MSP protein of the nanodiscs is revealed by an anti-His antibody conjugated with HRP ($1/10,000$). MW is the molecular weight marker (kDa). P Ctrl the RHD protein produced in the presence of Brij 35, N Ctrl: nanodiscs alone.

Figure 7:
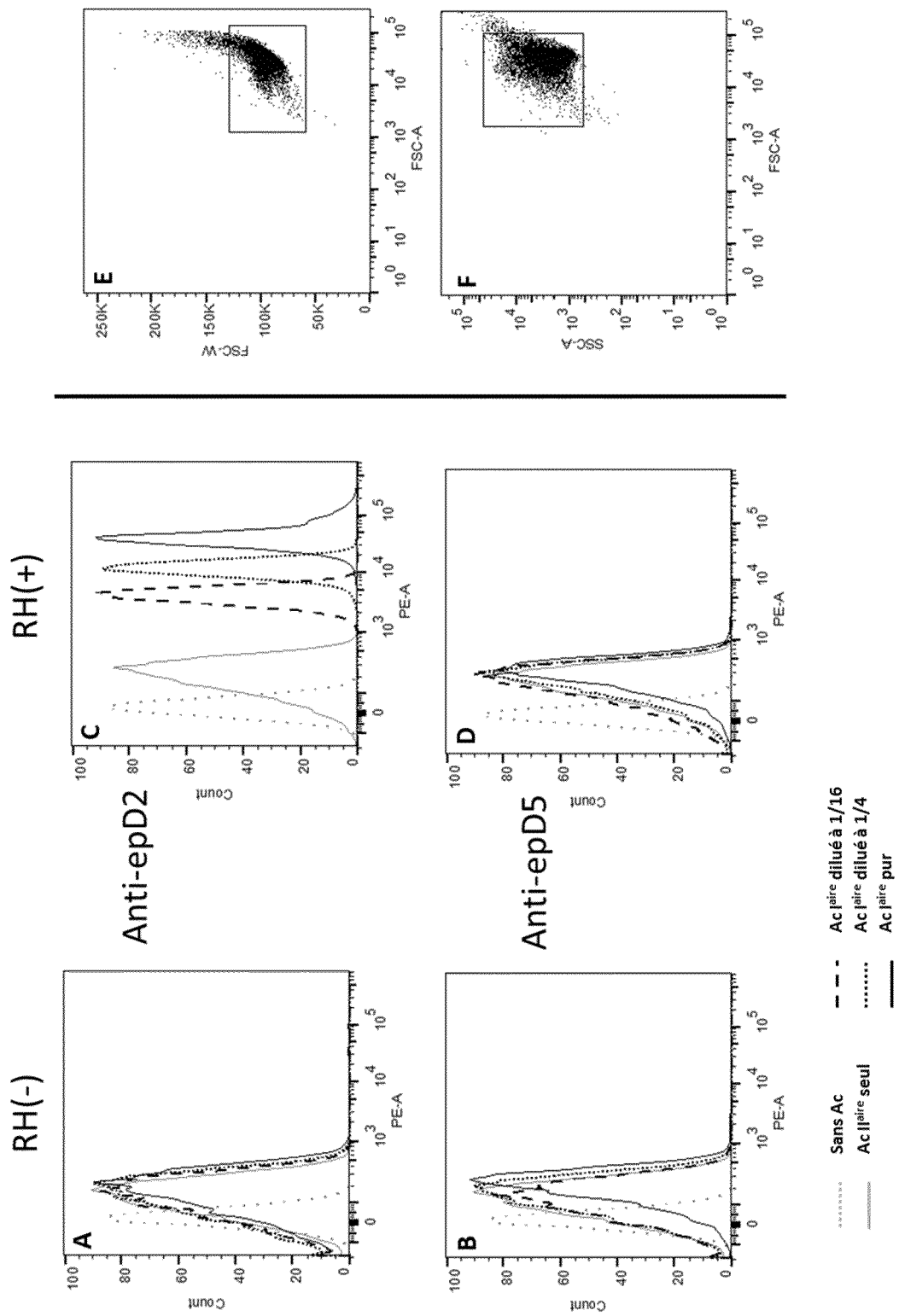

FIG. 7. Demonstration of the recognition of the RHD protein by different antibodies: Flow cytometry was performed on red blood cells incubated with different antibodies. (A)(B) Quantitative analysis of the recognition by the anti-ep D2 and anti-ep D5 antibodies of Rh (−) red blood cells used as negative control. (C)(D) Quantitative analysis of the recognition of Rh (+) red blood cells by the anti-ep D2 and anti-ep D5 antibodies. (E)(F) Selection of populations and sub populations studied.

EXAMPLES

Materials and Methods
I. Materials
The RTS 100 *E. coli* HY Kit stored at −20° C. is provided by 5 PRIME. The MSP1E3D1-His_POPC nanodiscs (500 µM) stored at −80° C. come from Cube Biotech. ELISA plates used are of the Nunc MaxiSorp 96-well type (Dutscher) and the FACS plates are from Corning. The A sepharose 4B protein resin comes from GE Healthcare Life Sciences. The Agarose HA resin and detergents ($C_{12}E_8$, Brij 35, Brij 58) at 20% and stored at −20° C. were obtained from Sigma-Aldrich.

The MPC8 rabbit polyclonal antibody recognizes residues 408-416 of the C-terminal of the RHD protein (Apoil et al., 1997), while the LOR-15C9 antibody is a monoclonal antibody (Apoil et al., 1997) which recognizes residues 320-331 and 350-354 of the RHD protein. Secondary antibodies conjugated with HRP (Horse Radish Peroxidase) directed against human IgG were obtained from P.A.R.I.S (Western Blot) and Jackson (ELISA). A murine Anti Penta-His antibody conjugated with HRP is supplied with the kit (RGS-His HRP Conjugate kit) from Qiagen. A goat anti-human IgG antibody is conjugated with R-Phycoerythrin (PE) (Beckman).

A pIVEX-HA custom vector has been developed for RHD protein expression in an acellular system. It was generated by substituting the His tag of the vector pIVEX2.3d (5 PRIME) with an HA tag, which allows a protein fused to an HA-tag in C-terminal to be obtained.

II. Methods

II.1. Acellular Protein Expression

The principle of in vitro protein expression is to introduce plasmid DNA containing the open reading frame encoding the protein of interest, in a reaction medium containing the elements necessary for protein synthesis. All transcriptional and translational machinery is provided by the E. coli S30 cell lysate.

Two types of systems were used. A first system in which all components are mixed in a single compartment ("batch" method) was used to screen the different expression conditions. A second system is the CECF (Continuous Exchange Cell Free) (Shirokov et al., 2007), where protein synthesis takes place in a compartment, separated from a reservoir by a semi-permeable membrane, allowing waste products to be diluted and substrates to be provided. The CECF system was used for the large-scale production of protein as continuous protein expression for up to 24 hours provides better yield as compared to the "batch" system.

II.1.A Protein Expression in "Batch" System

The experimental protocol developed by the 5PRIME company enables protein to be synthesized on a small scale in a volume of 50 µl in the RTS 100 E. coli HY Kit. The RTS 100 kit and the MSP1E3D1-His_POPC nanodiscs (500 µM) or 20% detergent ($C_{12}E_8$, Brij 35, Brij 58) are thawed on ice. The reaction mixture (12 µl E. coli lysate; Energy mix 10 µl; amino acids 12 µl; Methionine 1 µl; Reconstitution Buffer 5 µl) necessary for RhD protein production in the presence of nanodiscs is prepared in an Eppendorf tube at room temperature. The 50 µl mixture is then incubated with stirring in an Eppendorf thermomixer at 30° C., 750 rpm for 5 hours.

After expression, the mixture is centrifuged for 10 minutes at 22,000 g at 4° C. to separate the soluble fraction (the supernatant) from the insoluble fraction (the pellet).

II.1.B Protein Expression in CECF System

The CECF system was used for protein production in the presence of detergent or nanodiscs in a large volume (1-2 mL). The reactions were performed using the proportions shown in the appendix.

II.2. Purification

II.2.A Immunoprecipitation with HA Agarose

To immunoprecipitate the RHD-HA protein produced in the presence of detergent (condition 1) or nanodiscs (condition 2) (Table 1), 1 ml of the soluble fraction of the in vitro production is added to 250 µl (1 CV) of anti-HA agarose beads pre-washed with buffer $A_1$ or $A_2$. The tube is incubated under rotation at 4° C. overnight. The non-retained fraction is then recovered by centrifugation at 2,000 g for 10 minutes at 4° C. Subsequently, several washes are performed with buffer $A_1$ or $A_2$ (18 CV) and then with buffer $B_1$ or $B_2$ (28 CV). To perform these washes, the tubes were centrifuged at 5,200 g for 5 min at 4° C., and the supernatant is removed. After the last wash, the beads to which the proteins are bound are resuspended and incubated with rotation for 4 hours at 4° C. in 325 µl of $C_1$ or $C_2$ elution buffer. The eluate is recovered after centrifugation for 15 min at 18,000 g at 4° C.

II.2.B Immunoprecipitation with Protein A Sepharose 4B

On ice in an Eppendorf tube, 30 µl of the soluble fraction of the in vitro production is diluted to ⅕ in $A_3$ buffer (Table 3) and then incubated with 10 µl of purified MPC8 antibody (1.5 mg/ml) overnight at 4° C. on the wheel. The complex formed is then incubated for 1 hour at 4° C. on the wheel with 50 µl of protein A sepharose 4B resin previously washed with $A_3$ buffer.

The unretained fraction was recovered after centrifugation at 15,000 g for 5 minutes at 4° C. with low deceleration. The pellet is then washed 3 times by centrifugation with 1 mL of $A_3$ buffer, then 2 washes with $B_3$ buffer, and a final wash with $C_3$ buffer. To elute the protein, the resin is heated for 5 minutes at 100° C. with 50 µl of Laemmli 2×. After centrifugation at 15,000 g for 5 minutes, the eluate is recovered.

TABLE 1

Buffers used for the purification of the RHD protein.

| | Agarose HA | | Protein Sepharose |
|---|---|---|---|
| | Protein in the presence of detergent | Protein in the presence of nanodiscs | 4B Protein in the presence of nanodiscs |
| $A_1, A_2, A_3$ Buffers | 10 mM Hepes, 150 mM NaCl, pH 6.8 (0.3% C12E8) | 50 mM TrisHCl, 150 mM NaCl, pH 7.4 | PBS, 0.5% BSA, 5 mM EDTA |
| $B_1, B_2, B_3$ Buffers | 10 mM Hepes, 50 mM $K_2SO_4$, pH 6.8 (0.3% C12E8) | 20 mM Tris HCl, 100 mM NaCl, pH 7.4 | PBS, 0.5% BSA, 5 mM EDTA, 10 mM NaCl |
| $C_1, C_2, C_3$ Buffers | TpB + peptide HA (5 mg/1300 µl) 1% glycerol, pH 6.8 | TpB, peptide HA (5 mg/1300 µl), pH 6.8 | PBS, 5 mM EDTA |

II.3. Sucrose Gradient

The synthesis product was loaded onto a discontinuous sucrose gradient (5-10-15 20-30% in PBS), followed by ultracentrifugation at 210,000 g for 18 h at 4° C., using the conditions described by T H. Bayburt et al, 2007. The 0.5 ml fractions were collected from top to bottom and analyzed by Western blotting.

II.4. Electrophoresis

The samples are denatured in loading buffer (5 mM Tris-HCl, 8.56% sucrose, 1% SDS, 5% β-mercaptoethanol) and loaded onto a 10% denaturing polyacrylamide gel or 4-12% gradient Bis-Tris polyacrylamide gel (Invitrogen). The proteins are separated according to their molecular weight by electrophoresis at 180V in migration buffer (25 mM Tris-HCl, 192 mM Glycine, 0.1% SDS or 50 mM MOPS, 50 mM Tris HCl, 0.1% SDS, 1 mM EDTA).

II.5. Staining with Silver Nitrate

After incubation in fixation buffer (50% Methanol, 12% Acetic acid, 0.05% formaldehyde) with agitation for 1 hour, followed by several rinses in 50% Ethanol, the gel is treated with a 1% Sodium thiosulfate solution for 1 minute. After several rinses in water, the gel is incubated for 20 min in the staining mixture (0.2% $AgNO_3$, 0.075% Formaldehyde). After two rinses in water, a developing solution (0.05% formaldehyde, 0.04% thiosulfate, 6% $Na_2CO_3$), reveals the proteins on the gel. The reaction was quenched by a 10% acetic acid solution for 30 minutes.

II.6. Western-Blot

Once migration is complete, proteins were transferred onto a nitrocellulose membrane (Amersham) for 2 hours at 30V in a transfer buffer (12.5 mM Tris-HCl, 96 mM Glycine, 20% Ethanol).

II.6.A Revelation of the RHD Protein

After transfer, the membrane is washed once with PBS alone and then saturated in a solution of PBS containing diluted 5% milk for 1 hour at room temperature with agitation. The membrane is then incubated with the primary LOR-15C9 antibody overnight at 4° C. on a rotating plate.

After several washes in 0.1% PBS-Tween20, the membrane is incubated for 1 hour in the presence of the murine anti-human IgG secondary antibody conjugated with HRP diluted to 1/800 in PBS 5% milk with agitation. After several washes in 0.1% PBS-Tween20 followed by PBS alone, the enzymatic reaction is revealed by chemiluminescence (GE Healthcare Life Sciences).

II.6.B Revelation of the MSP Protein of the Nanodiscs

The MSP protein of the nanodiscs, which carries a Poly-Histidine Tag is revealed by Western blotting with the anti-His antibody conjugated with HRP (Qiagen).

After transfer, the membrane is rinsed twice with TBS alone then blocked for 1 hour at room temperature in the freshly prepared blocking solution according to the protocol supplied with the kit. After 2 washes in TBS-0.05% Tween20 at room temperature and a final wash in TBS alone, the membrane is incubated for 1 hour at room temperature with the anti-Penta-His-HRP antibody diluted to 1/10,000 in the blocking solution. After several washes in TBS-0.05% Tween20 and TBS alone, the enzymatic reaction is revealed by chemiluminescence.

II.7. Flow Cytometry

Recognition of the RHD protein by various anti-epD human monoclonal antibodies is revealed by indirect tagging on red blood cells.

For this, 0.5 µl of the pellet of red blood cells ($5 \times 10^6$ cells) was suspended in 1 ml of 0.2% BSA-PBS and then distributed in the different wells of a plate, in an amount of $5 \times 10^5$ cells/well. The plate is centrifuged for 3 minutes at 100 g at 4° C. and the supernatant is removed.

After the first washing, the red blood cells are incubated for 1 h at 4° C. with antibodies directed against the RHD protein. The cells are then washed twice in 0.2% BSA in PBS and incubated in the dark for 1 h at 4° C. with human anti-IgG antibody conjugated with R-Phycoerythrin (PE) diluted to 1/100 in 0.2% BSA-PBS. After 3 washes in 0.2% BSA-PBS, cells are resuspended in 200 µl PBS and analyzed by flow cytometry (BD FCS Canto II, BD Biosciences).

The results are analyzed by the FlowJo software.

II.8. ELISA Test

To reveal the interaction between the various antibodies and the protein of interest, a ELISA sandwich test was performed.

The MPC8 capture antibody is incubated in the wells in PBS at 1 ng/µl per well. The capture is done overnight at room temperature. After several washes in PBS, the wells are then saturated with 5% milk-PBS and then rinsed with PBS.

RHD protein produced in vitro in the presence of nanodiscs is then added for 45 minutes at 37° C. in the wells. After rinsing in PBS, anti-RHD human antibodies to be tested are incubated with this complex for 45 minutes at 37° C., the excess is eliminated by successive washes.

The formed complexes are detected using an anti-human IgG antibody (1/50,000 in PBS), depleted against mouse and rabbit IgG and conjugated with HRP. The entirety is incubated at 37° C. for 30 minutes. After washing, the complex bound to the enzyme is revealed by the addition of TMB (Bio-Rad) in the wells. The reaction is quenched with a solution of 0.1 N $H_2SO_4$ and the absorbance is measured at a wavelength of 450 nm.

Results

I. Expression and Solubility Test of the RHD Protein in the Presence of Detergent We have studied the compatibility of different detergents with the production of the RHD protein in the translation system in vitro.

Three non-ionic detergents are used, $C_{12}E_8$, Brij 35, Brij 58. The choice of these detergents was made based on their non-denaturing nature on membrane proteins. The concentration used was chosen based on their low critical micelle concentration (CMC concentration at which micelles are formed), (0.11% for Brij 35, 0.0086% for Brij 58 and 0.006% for $C_{12}E_8$). An analysis by Western blotting for "batch" productions of the RHD protein in the presence of the 3 detergents (0.5% $C_{12}E_8$, 0.5% Brij 35, 0.5% Brij 58) (FIG. 1) has shown the presence of the protein only in the soluble fractions for reactions containing Brij 35 or Brij 58. For the reaction containing $C_{12}E_8$, only a low intensity signal was detected in the insoluble fraction, whereas in the absence of detergent, the protein is mainly found in the pellet (insoluble fraction). $C_{12}E_8$ is therefore not conducive to the expression of the RHD protein in in vitro synthesis. Brij 35 thus proves to be the most compatible detergent for the production of the RHD protein. Therefore, this detergent was selected to produce the protein on a larger scale.

I.1. Large-Scale Production and Purification of the RHD Protein in the Presence of Detergent Once the optimum expression and solubility conditions are established, a large-scale production in 2 ml reaction volume is performed using the CECF system in the presence of the selected detergent (0.5% Brij 35). The soluble fraction is purified on the basis of the recognition, by Agarose-HA resin, of the HA tag fused to the protein. Elution is achieved by competition with the HA peptide. The entire purification is carried out by substituting Brij 35 with 0.3% $C_{12}E_8$, detergent previously used successfully by the team for the purification and the functional reconstitution of the RHCG protein in liposomes (Mouro-Chanteloup and al. 2010), a homologous non-erythrocyte Rh protein.

The results shown in FIG. 2 indicate that the soluble RHD protein is mainly found in the eluate and elution washing. It is also observed that a portion of the protein is not fixed to the resin, and is found in the unretained fraction (NR). Analysis of the eluate in silver nitrate shows that it contains only RHD protein. The reaction time selected for the production of soluble RHD protein is 8 hours of reaction, as there is a risk of aggregation of the RHD protein from 16 hours of reaction.

II. Expression and Solubility Test of the RHD Protein in the Presence of Nanodiscs We studied the effect of nanodiscs the level of expression of the RHD protein. The protein is produced in the presence of different concentrations of nanodiscs (e.g. MSP1E3D1-His_POPC (20, 40, 60, 80 µM).

The synthesis products of each production are analyzed by Western blotting. As with the protein produced in the presence of 0.5% Brij 35, most of the protein produced in the presence of nanodiscs is localized in the soluble fractions (FIG. 3). The presence of nanodiscs at concentrations of 20, 40, 60 µM make it possible to obtain synthesis yields as high as in the presence of Brij 35. However, the presence of a large concentration of nanodiscs (80 µM) causes reduced synthesis. As expected, the signal intensity of MSP protein in the soluble fraction increases with the concentration of nanodiscs. We also note that the migration patterns of the soluble and insoluble fraction are different, this difference being due to the presence of polymers in the E. coli lysate as reported in the protocol provided with the RTS 100 kit.

II.1 Large-Scale Production of the RHD Protein in the Presence of Nanodiscs (CECF)

Two large-scale productions were carried out in a final volume of 1 ml in the presence of nanodiscs at a concentration of 50 µM. This concentration appears, according to the small-scale expression tests, suitable for the production of RHD protein with a good yield. A production control in the presence of 0.5% Brij 35 was performed in parallel. Analysis of constructs by Western blotting shows that the RHD protein is produced essentially in the soluble fraction and the nanodiscs. A greater deposit of nanodiscs in the insoluble fraction is noted, suggesting formation of aggregates (FIG. 4).

III. Different Approaches of Purification of the RHD Protein Produced in the Presence of Nanodiscs As for the production in the presence of detergent, the protein produced in the presence of nanodiscs is found in the soluble fraction also containing several bacterial lysate proteins of E. coli. Its purification is therefore necessary, as well as the separation of full nanodiscs (in which the protein has been inserted) from empty nanodiscs. Two approaches have been used to purify the RHD protein inserted in nanodiscs. The first approach is to immunoprecipitate the RHD protein using two protocols, the second approach is the ultra-centrifugation of the synthesis product in a sucrose gradient (Bayburt et al., 2007).

The first immunoprecipitation method tested consists of retaining the RHD protein fused with an HA tag with an HA agarose resin. Elution is carried out in the presence of HA peptide, which detaches the RHD protein by competition.

In the second protocol, the protein is immunoprecipitated using a protein A sepharose 4B resin. The in vitro production is contacted with a rabbit anti-RH polyclonal antibody (MPC8), the complex is then incubated with the protein A Sepharose 4B resin which fixes the antibody complexed to the protein. At the end, the protein is eluted by heating in the presence of Laemmli buffer.

In the elution fractions of the 2 protocols, nanodiscs were co-eluted with the RHD protein, although there is a low yield with loss during the different stages of purification as observed by Western blotting (FIG. 5).

According to the immunoprecipitation results, the RHD protein and the nanodiscs are found in the eluate, which indicates an insertion of the protein in nanodiscs.

This result was also found by a sucrose gradient analysis of the synthesis product. Samples from the first 11 fractions were collected from top to bottom and then analyzed by Western blotting (FIG. 6). It is noted that the RHD protein and the MSP protein of the nanodiscs are in the same fractions 6-11, corresponding to a concentration of 10-15% sucrose, while the empty nanodiscs which are in the minority are in the higher fractions (4-5).

IV. Immunoassay of RHD Protein Antigens Produced in the Presence of Nanodiscs To verify the conformation of the protein translated in vitro in the presence of detergent, we wished to develop a "sandwich ELISA" test using conformational monoclonal antibodies (anti-ep D) directed against the 9 D epitopes, according to the Tippett classification. These antibodies recognize the protein only in its native form, and thus their reactivity depends on the conformation of said protein. The non-conformational LOR-15C9 antibody is also used in this test as a positive control.

IV.1. Test of Antibodies by Flow Cytometry

Before the development of this ELISA test, supernatants from different laboratories and containing anti-ep D antibodies of the unknown concentration were analyzed by flow cytometry on red blood cells expressing the RHD protein. Several dilutions were tested (pure, ¼, ¹/₁₆) and RHD (−) red blood cells were used as a negative control (FIG. 7A-B).

The results show that conformational antibodies or not, recognize different epitopes of the RHD protein according to their concentrations (FIG. 7C). The analysis was performed in the "single cell" sub-populations to eliminate clustered cells. The results also show a high homogeneity within the test sample studied (FIG. 7E-F).

V. Development of the ELISA Test

After determining the dilution at which the antibodies will be used to perform an ELISA test, other parameters must be optimized such as the choice of the capture antibody and plate blocking.

As capture antibodies, we have the choice of anti-HA or MPC8. However, the anti-HA may only be used on crude fractions and not on the protein purified by immunoprecipitation with HA agarose. Indeed the presence of the HA peptide in the elution fraction can greatly reduce the sensitivity of the test. Therefore, we retained MPC8 as the capture antibody, which can be used with all crude or purified fractions.

Different dilutions of the product synthesized in the presence of 40 µM of nanodiscs were used in a first ELISA test (¹/₄₀, ¹/₈₀, ¹/₁₆₀) in duplicate, with the various previously optimized conditions, using the LOR-15C9 antibody as the primary antibody at ¹/₃₂ (table 2), and an anti-human conjugated antibody. Control wells were carried out in the absence of the protein or of the LOR-15C9 primary antibody.

In Table 2, the signal intensity in the test wells increases with protein concentration. This intensity is higher than that of the control wells despite the background noise.

TABLE 2

ELISA test results of different dilutions of the synthesis product of the RHD protein inserted into nanodiscs.

| OD | Control wells | | Test wells | | | | | |
|---|---|---|---|---|---|---|---|---|
| | Protein(-) | Primary Ab(-) | Protein | 1/40 | Protein | 1/80 | Protein | 1/160 |
| 450 nm | 0.129 | 0.143 | 0.2 | 0.247 | 0.214 | 0.208 | 0.124 | 0.143 |

BIBLIOGRAPHIC REFERENCES

Apoil, P. A., M. E. Reid, G. Halverson, I. Mouro, Y. Colin, F. Roubinet, J. P. Cartron, and A. Blancher. 1997. A human monoclonal anti-D antibody which detects a non-conformation-dependent epitope on the RhD protein by immunoblot. Br J Haematol 98:365-374.

Avent, N. D., and M. E. Reid. 2000, The Rh blood group system: a review. Blood 95(2): 375-387, Bayburt, T. H., A. J. Leitz, G. Xie, D. D. Oprian, and S. G. Sligar. 2007. Transducin activation by nanoscale lipid bilayers containing one and two rhodopsins. J Biol Chem 282:14875-14881.

Carlson, E. D., R. Gan, C. E. Hodgman, and M. C. Jewett. 2012 Cell-Free Protein Synthesis: Applications Come of Age, Biotechnol Adv. 30(5): 1185 □1194.

Cartron, J. P. 1999. RH blood group system and molecular basis of Rh-deficiency. Baillieres Best Pract Res Clin Haematol 12:655-689.

Cartron, J. P., C. Rouillac, C. Le Van Kim, I. Mouro, and Y. Colin. 1996. Tentative model for the mapping of D epitopes on the RhD polypeptide. Transfus Clin Biol 3:497-503.

Denisov, I. G., Y. V. Grinkova, A. A. Lazarides, and S. G. Sligar. 2004. Directed self-assembly of monodisperse phospholipid bilayer Nanodiscs with controlled size. J Am Chem Soc 126:3477-3487.

Goossens D, da Silva N, Metral S, Cortes U, Callebaut I, Picot J, Mouro-Chanteloup I, Cartron J P. 2013. Mice expressing RHAG and RHD human blood group genes. PLoS One 8(11):e80460. Grinkova, Y. V., I. G. Denisov, and S. G. Sligar. 2010 Engineering extended membrane scaffold proteins for self-assembly of soluble nanoscale lipid bilayers. Protein Eng Des Sel. 23(11): 843-848.

Mouro-Chanteloup, I., S. Cochet, M. Chami, S. Genetet, N. Zidi-Yahiaoui, A. Engel, Y. Colin, O. Bertrand, and P. Ripoche. 2010. Functional reconstitution into liposomes of purified human RhCG ammonia channel. PLoS One 5:e8921.

Mouro-Chanteloup, I., A. M. D □Ambrosio, P. Gane, C. Le Van Kim, V. Raynal, D. Dhermy, J. P. Cartron, and Y. Colin. 2002. Cell-surface expression of RhD blood group polypeptide is posttranscriptionally regulated by the RhAG glycoprotein. Blood 100:1038-1047.

Mouro, I., Y. Colin, B. Cherif-Zahar, J. P. Cartron, and C. Le Van Kim. 1993. Molecular genetic basis of the human Rhesus blood group system. Nat Genet 5:62-65.

Rogé, J., and J. M. Betton. 2005 Use of pIVEX plasmids for protein overproduction in *Escherichia coli*, Microb Cell Fact. 4: 18.

Shirokov, V. A., A. Kommer, V. A. Kolb, and A. S. Spirin. 2007. Continuous-exchange protein-synthesizing systems. Methods Mol Biol 375:19-55.

Tippett, P., C. Lomas-Francis, and M. Wallace. 1996. The Rh antigen D: partial D antigens and associated low incidence antigens. Vox Sang 70:123-131.

The invention claimed is:

1. A method of synthesizing an erythrocyte protein in its native form selected from RhD of SEQ ID NO: 5, RhCE of SEQ ID NO: 6, RhAG of SEQ ID NO: 7 and UTB of SEQ ID NO: 8, or a variant thereof, said method comprising the steps of:
   a) contacting a nucleic acid encoding said protein or a variant having at least 95% identity therewith with an acellular protein production system, in the presence of at least one non-ionic detergent selected from Brij-35 and Brij-58, liposomes or nanodiscs; and
   b) synthesizing said protein,
wherein step a) occurs either during or before step b).

2. The method according to claim 1, wherein the contacting according to step a) occurs in the presence of nanodiscs comprising a MSP protein selected from proteins of SEQ ID NO: 9, 10 or 11.

3. The method of claim 2, wherein said MSP protein is fused to a tag sequence.

4. The method according to claim 1, wherein the acellular system for protein production is a batch system or an acellular system with continuous exchange.

5. The method according to claim 1, wherein the concentration in nanodiscs is less than 80 μM.

6. The method according claim 1, wherein said erythrocyte protein, or variant thereof is fused to a tag sequence.

7. The method of claim 1 further comprising a step of recovering the erythrocyte protein or variant thereof.

8. The method of claim 1 further comprising a step of fixing the erythrocyte protein or variant thereof to a solid support.

9. The method of claim 1, wherein said nanodiscs comprise of one or more phospholipids selected from among dioleoylphosphocholine, dimyristoylphosphocholine, and palmitoyl oleoyl-glycero-phosphocholine.

10. The method of claim 1, wherein said non-ionic detergent is used at a concentration comprised between 0.1% and 5%.

11. The method of claim 1, wherein said non-ionic detergent is used at a concentration of 0.5%.

* * * * *